United States Patent [19]

Prendergast

[11] Patent Number: 5,681,831
[45] Date of Patent: Oct. 28, 1997

[54] METHOD OF TREATING VIRAL AND RETROVIRAL INFECTIONS INCLUDING HIV BY ADMINISTRATION OF $N^6$-($\Delta$)$^2$-ISOPENTENYL) ADENOSINE OR AN ANALOGUE THEREOF

[76] Inventor: Patrick T. Prendergast, Baybush, Straffan, County Kildare, Ireland

[21] Appl. No.: 251,659

[22] Filed: May 31, 1994

Related U.S. Application Data

[63] Continuation of Ser. No. 26,196, Feb. 26, 1993, abandoned, which is a continuation of Ser. No. 747,438, Aug. 14, 1991, abandoned, which is a continuation of Ser. No. 362,820, Jun. 7, 1989, abandoned.

Foreign Application Priority Data

Aug. 25, 1988 [IE] Ireland .................... 2585/88

[51] Int. Cl.$^6$ .................................................. A61K 31/70
[52] U.S. Cl. ..................... 514/46; 514/47; 536/26.7; 536/27.63; 536/27.62; 536/26.23; 536/26.26
[58] Field of Search .................... 514/46, 47; 536/26.13, 536/26.23, 26.26, 26.7, 27.62, 27.63

[56] References Cited

U.S. PATENT DOCUMENTS

| | | | |
|---|---|---|---|
| 3,666,856 | 5/1972 | Elion et al. | 514/46 |
| 3,758,684 | 9/1973 | Elion et al. | 514/46 |
| 3,851,056 | 11/1974 | Stork et al. | 514/46 |
| 3,966,916 | 6/1976 | Kampe et al. | 514/46 |
| 4,007,177 | 2/1977 | Emanuel | 544/266 |
| 4,016,262 | 4/1977 | Fauland et al. | 514/46 |
| 4,464,361 | 8/1984 | Ohki et al. | 514/46 |
| 4,558,051 | 12/1985 | Sunshine | 514/261 |
| 4,605,644 | 8/1986 | Foker | 514/45 |
| 4,657,897 | 4/1987 | Bristol et al. | 514/47 |
| 4,687,733 | 8/1987 | Trewyn et al. | 435/7 |
| 4,791,103 | 12/1988 | Trivedi et al. | 514/46 |
| 4,843,066 | 6/1989 | Yamada et al. | 514/45 |
| 5,292,725 | 3/1994 | Prendergast | 514/46 |

FOREIGN PATENT DOCUMENTS

| | | |
|---|---|---|
| 14444/88 | 10/1988 | Australia. |
| 0 286 418 | 10/1988 | European Pat. Off. . |
| 2845 | 3/1966 | France. |
| 2079150 | 1/1982 | United Kingdom .................... 514/46 |
| 8 912 380 | 12/1989 | WIPO. |

OTHER PUBLICATIONS

Burrows et al., "The Isolation and Identification of Two Cytokinins from *Escherichia coli* Transfer Ribonucleic Acids," Biochemistry, 8 (7), 307 1–3076 (1969).

(List continued on next page.)

*Primary Examiner*—John Kight
*Assistant Examiner*—L. Eric Crane
*Attorney, Agent, or Firm*—Fish & Richardson PC

[57] ABSTRACT

Pharmaceutical formulations of compounds and drugs for treatment against viruses and prions (proteinaceous infectious particles), e.g., CMV, Herpes Simplex, Hepatitis B, Scapie Creutzfeldt-Jakob Disease, in particular for drug treatment of persons and animals suffering from certain retroviral infections, and of person suffering from infection by retroviruses related to human immuno-deficiency viruses (HIV), and for prophylactic drug treatment of persons who may be suffering from such infections. The anti-viral pharmaceutical formulations according to the invention have the general formula:

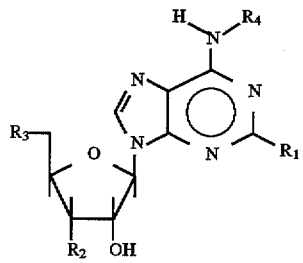

21 Claims, 23 Drawing Sheets

OTHER PUBLICATIONS

Woodsworth et al., "Characterization of Monoclonal Antibodies Specific for Isopentenyl Adenosine Derivatives Occurring in Transfer RNA," *Biochem. Biophys, Res. Comm.*, 114(2), 791–796 (1983).

Hecht et al., "Cytokinins: Influence of Side-Chain Planarity on $N^6$-Substituted Adenines and Adenosines on Their Activity in Promoting Cell Growth," Phytochemistry, 9, 1907–1913 (1970).

Shaw et al., "Purine, Pyrimidines, and Imidazoles. Part XXIV. Synthesis of Zeatin, a Naturally Occurring Adenine Derivative with Plant Cell-division-promoting Activity, and Its 9-β-D-Ribofuranoside," *J. Chem. Soc., Part C*, 1966.921–924.

Burrows et al., "Cytokinin from Soluble RNA of *Escherichia coli*: 6-(3-Methyl-2-butenylamino)-2-methylthio-9-β-D-ribofuranosylpurine," *Science*, 161, 691–693 (1968).

Vold et al., "Urine Levels of N-[9-(β-D-Ribofuranosyl)purin-6-ylcarbamoyl]-L-threonine, $N^6$-($\Delta^2$-Isopentenyl)adenosine, and 2'-O-Methylguanosine as Determined by Radioimmunoassay for Normal Subjects and Cancer Patients," *Cancer Research*, 42. 5265–5269 (1982).

Bratslavskaya et al., "Study of the Mechanism of Inhibition of Moloney's Mouse Sarcoma Virus by $N^6$-($\Delta^2$-Isopentenyl)-adenosine," *Onkornavirusy i Nesoetsifich. Rezistentnost Organizma*, 1978, 29–33; Chem/ Abstr., 90(11), p. 34, Abstr. No. 80810k (1979).

Gallo et al., "$N^6$-($\Delta^2$-Isopentenyl) Adenosine: The Regulatory Effects of a Cytokinin and Modified Nucleoside from t-RNA on Human Lymphocytes," *Biochimica et Biophysica Acta*. 281, 488–500 (1972).

Milo et al., "Effect of Cytokinins on Tobacco Mosaic Virus Production in Local-Lesion and Systemic Hosts," *Virology*, 38, 26–31 (1969).

Brown, "Survivors Offer Lessons in Resisting HIV—Key to 'Non-Progression' May Be Within Individuals," *New York Times*, Aug. 10, 1994, p. A3.

The Merck Index, "An Encyclopedia of Chemicals and Drugs", Ninth Edition, No. 141 (p. 20), No. 4791 (p. 648), No. 9538 (p. 1267).

Brazilian Journal of Medical and Biological Research, vol. 20, No. 1, 1987, pp. 1–10; R.C. Guimaraes et al.: "Purine base uptake in Trypanosoma cruzi: adaptations and effects of inhibitors".

Experimental Parasitology, Vol. 66, No–2, Aug. 1988, pp. 189–196; D.R. Taylor et al.: "Leishmania mexicana amazonensis: ADP-ribosyltransferase antagonists specifically inhibit promastigote differentiation".

Experimental Parasitology, vol. 56, No. 3, Dec. 1983, pp. 409–415; G.T. Williams: "Trypanosoma cruzi: inhibition".

T. Roosevelt: "The synthesis and some properties of polynucleotides containing N6-(Δ-2-isopentenyl)-adenosine".

Biochemistry International, vol. 9, No. 2, Aug. 1984, pp. 207–218; L.L. Nolan et al.: "The effect of formycin B on mRNA translation and uptake of purine precursors in Leishmania mexicana".

Experimental Parasitology, vol. 56, No. 2, Oct. 1983, pp. 236–240; J.L. Avila et al.: "Trypanosoma cruzi: 4-aminopyrazolopyrimmide in the treatment of experimental chagas' disease".

Journal of Heterocyclic Chemistry, vol. 20, No. 2, Mar.–Apr. 1983, pp. 295–299; M.P. Lamontagne et al.: "Preparation of 7-substituted pyrrolo(2,3-d)pyrimidines and 9-substituted purines as potential antiparasitic agents".

The Journal of Immunology, vol. 129, No. 6, Dec. 1982, pp. 2759–2762; J.J. Wirth et al.: "Inhibitory action of elevated levels of adenosine-3':5' cyclic monophosphate on phagocytosis: effects on macrophage-Trypanosoma cruzi interaction".

International Journal of Pharmaceutics, vol. 65, Nos. 1–2, 1990, pp. 57–62; B. Chaudhuri et al.: "Polyether polyurethane delivery systems. II: Effect of coadministration of pentostatin with N6-(Δ-2-isopentenyl) adenosine".

Windholz et al. (eds.), *Merck Index, 10th Ed.*, Merck & Co., Rahway, NJ, 1983, pp. 22–23, See Entry No. 142.

R. Thedford, "The Synthesis and Some Properties of Polynucleotides Containing $N^6$-(Δ-2-isopentenyl)-adenosine," *Diss. Abstr. Int. B*, 34(2), 528–529 (1973).

Kampe et al., "Coronary Dilating $N^6$-Benzyladenosines," Patent No. 2,007,273 (W. Ger.), Aug. 26, 1971; *Chem. Abstr.*, 75. p. 347, Abstr. No. 141121a (1971); only Abstract supplied.

R. S. Root–Bernstein(I), "AIDS IS More Than HIV: Part I," *Genetic Engineering News*, Sep 1, 1992, pp. 4–6.

R. S. Root–Bernstein(II), "AIDS IS More Than HIV: Part II," *Genetic Engineering News*, Sep 15, 1992, pp. 4–5.

METHOD OF TREATING VIRAL AND RETROVIRAL INFECTIONS INCLUDING HIV BY ADMINISTRATION OF $N^6$-($\Delta$)$^2$-ISOPENTENYL) ADENOSINE OR AN ANALOGUE THEREOF The application is a continuation of U.S. Ser. No. 08/026,196, filed Feb. 26, 1993, now abandoned, which is a continuation of U.S. Ser. No. 07/747,438, filed Aug. 14, 1991, now abandoned, which is a continuation of U.S. Ser. No. 07/362,820, filed Jun. 7, 1989, now abandoned.

FIELD OF THE INVENTION

This invention relates to methods of treatment against viruses and prions (proteinaceous infectious particles) e.g., CMV, Herpes Simplex, Hepatitis B, Scapie Creutzfeldt-Jakob Disease. Particularly, the invention relates to methods of drug treatment of persons and animals suffering from certain retroviral infections, and of persons suffering from infection by retroviruses related to human immunodeficiency viruses (HIV) and to methods of prophylactic drug treatment of persons who may be suffering from such infections. More particularly, the invention relates to treatments for reducing levels of HIV virus in blood cells such as the monocyte/macrophage and T lymphocytes of the person being treated. The invention further relates to formulations of compounds and drugs to be used in such treatment methods.

BACKGROUND OF THE INVENTION

It is believed that human infection by the family of retroviruses known as HIV is deleterious to the health of infected persons. Examples of viruses which are currently believed to belong to the HIV family are the lymphadenopathy-associated virus (LAV) and the human T-lymphotrophic virus type III (HTLV-III). LAV and HTLV-III, which were discovered independently of each other, are now known to be the same virus and are referred to as HIV-I. Although much is known about modes of transmission of such viruses from person to person, (THE NATURAL HISTORY OF HIV INFECTION IN A COHORT OF HOMOSEXUAL AND BISEXUAL MEN: A DECADE OF FOLLOW UP. Nancy A. Hessol, G. W. Rutherford, A. R. Lifson, P. M. O'Malley, Dept. of Public Health, San Francisco, Calif.) there is currently controversy regarding particular interactions between the virus and the host cells in which they reside. Generally, a person who is infected by HIV develops antibodies to the virus and at some point, the immune system of the person becomes damaged and becomes ineffective in defending the body from diseases. This condition has come to be known as Acquired Immune Deficiency Syndrome, or AIDS. Eventually, because of the immune deficiency of his or her body, an AIDS patient is overcome by one or more of a group of opportunistic infections, for example, Kaposi's Sarcoma and pneumocystis.

There is evidence that macrophage/monocyte infection is a factor in the progression of HIV infection, in initiating the brain damage that is known to occur in AIDS patients, and in triggering the collapse of the immune system as evidenced by eventual profound depletion of T4 lymphocytes. It has been demonstrated using anti-HIV p24 antibody that monocyte/macrophages can be infected with HIV. Up to 70% of cells from individual donors could be infected (Crowe et al., AIDS Research and Human Retroviruses 3, No. 2, (1987) 135). Nicholson et al. have proposed an HIV-III/LAV-induced effect in monocyte function rather than (or in addition to) an intrinsic defect in surviving T cells to account for observed abnormalities in T cell assays that are monocyte-dependent such as pokeweed mitogen-induced antibody synthesis and proliferative responses to soluble antigens. These T cell assays have previously been reported as abnormal even when assayed as T cell subsets (The Journal of Immunology, 137, No. 1, (1986) 323).

Since it is well established that one of the first events that occurs when a foreign material (for example, a virus) enters the body is its uptake by mononuclear phagocytes, it is conceivable that these cells represent a primary target for HIV. Gartner et al. have shown that virus production by HTLV-III/LAV infected macrophages was high and long-lived, indicating that these cells may play a role in virus dissemination and persistence. They have demonstrated HTLV-III/LAV replication in macrophages was fully productive in the situations they evaluated (Science 233 (1986) 215).

Salahuddin et al. observed that in-vitro pulmonary macrophages can be infected with HTLV-III and appear to be less susceptible to the phytopathic effects of this retrovirus, which suggests that tissue macrophages should be considered as potential reservoirs of HTLV-III in-vivo (Blood 68, No. 1, (1986) 281).

Ho D. D. et al. observed normal blood-derived monocytes/macrophages were found to be susceptible to infection in-vitro by HTLV-III. In addition, HTLV-III was recovered from monocytes/macrophages of patients infected with this virus. It was postulated therefore that HTLV-III-infected monocyte/macrophages may serve as a vehicle for the dissemination of virus to target organs and as a reservoir for viral persistence, as has been shown for other lentiviruses, including visna virus and caprine arthritis encephalitis virus (J. Clin Invest. 77, (198)1712).

While an anti-viral agent which could kill all infecting HIV or completely inhibit its replication (and at the same time have an acceptable toxicity profile) is clearly desirable, the situation is that no such agent is at present available.

Anti-viral agents which inhibit replication of viruses have been known since the mid 1960's. (PROSPECTS FOR THE PREVENTION AND THERAPY OF INFECTIONS WITH THE HUMAN IMMUNODEFICIENCY VIRUS. Markus Vogt, Martin S. Hirsch. Infectious Disease Unit, Massachusetts General Hospital, Harvard Medical School, Boston). Several hundred or more of these agents are now known but azidothymidine (AZT, zidovudine) is the only drug which has received approval from the Federal Drug Administration in the United States for treatment against the virus of people with AIDS. The use of AZT in the treatment of AIDS patients suffers from many deficiencies. AZT is very expensive. Treatment with AZT often causes side effects in persons being treated with it and often the side effects are so severe that treatment with it must be halted altogether. (DEVELOPMENT OF HIV-VARIANTS WITH HIGHER RESISTANCE AGAINST AZT UNDER TREATMENT WITH AZT. F. Zimmermann, L. Biesert, H von Briesen, Klinikum der Universitat, Frankfurt, FRG.) The long term effectiveness of treatment with AZT of AIDS patients is still unknown, although it is believed that AZT treatment will not result in the elimination of the virus from the body of an infected person. There is evidence that AZT-resistant strains of HIV are developing in AIDS patients being treated with AZT (F. Zimmermann and L. Biesert).

There is thus a need for new, less expensive, less toxic and more effective treatments which work against HIV and more effective treatments which work against HIV in all cell types where the virus is resident, such as of monocyte/macrophage and T4 lymphocyte, Langerhan Cells which act as hosts for viral replication. These new therapies would preferably be virus non-specific so as to prevent the promotion of resistant strains.

As a further background to particular aspects of the present invention, the compound $N^6$-($\Delta$2-isopentenyl) adenosine, (IPA), which has formula Ia, illustrated below, has been used previously in clinical trials involving the treatment of cancer. (CYTOKININS AS CHEMOTHERAPEUTIC AGENTS. Annals of the New York Academy of Science, 25, 225–234 Mittleman,, Arnold, et al. (1975)). IPA is a naturally occurring compound. For example, it has been shown to be an anticodon-adjacent nucleoside in certain t-RNAs [$N^6$-($\Delta$2- ISOPENTENYL) ADENOSINE: THE REGULATORY EFFECTS OF A CYTOKININ AND MODIFIED NUCLEOSIDE FROM t-RNA ON HUMAN LYMPHOCYTES]. Biochimica et Biophysica Acta, 281:488–500. Gallo, Robert C., et al. (1972)). IPA has been shown to have cytokinin properties, (Mittleman, et al.) to inhibit the growth of human leukemic myeloblasts, to inhibit the growth of cultured lymphocytes stimulated by phytohemagglutinin (PHA) at certain concentrations and to stimulate the growth of cultured lymphocytes stimulated by PHA at lower concentrations (Gallo, et al.). Further, IPA has been used in clinical experiments on humans as a chemotherapeutic agent (Mittleman, et al.).

Other compounds, of formula Iq-It (illustrated below) are also known, and can be found in the following references:

Iq: W. J. Burrows, O. J. Armstrong, F. Skoog, S. M. Hecht, J. T. A. Boyle, N. J. Leonard and J. Occolowitz, Science, 161, (1968) 691.
W. J. Burrows, D. J. Armstrong, F. Skoog, S. M. Hecht, J. T. A. Boyle, N. J. Leonard and J. Occolowitz, Biochemistry, 8, (1969) 3071.
Ir: G. Shaw, B. M. Smallwood and D. V. Wilson, J. Chem. Soc.,C, (1966) 921.
Is: S. M. Hecht, Reference 29 in Gallo et al, Biochim et Biophysica Acta, 281, (1972) 488.
It: as for Is.

SUMMARY OF THE INVENTION

The present invention provides a method of treatment, therapeutic or prophylactic, against any viral infection and materials which may be used in such methods. Further the invention provides treatment for an organism infected with HIV. Certain embodiments of the invention provide methods of treating blood samples to reduce HIV levels relative to untreated samples.

Further, the invention provides a treatment to prevent alteration of morphology or function of a cell latently or actively infected by the HIV virus genome. Such an example would be the ability of IPA to prevent expression of the tat gene product in epidermal Langerhan cells and thus prevent or cause to regress resultant epidermal morphological abnormalities and tumours in patients infected with HIV.

The present invention provides a method of use for compounds of general formula I.

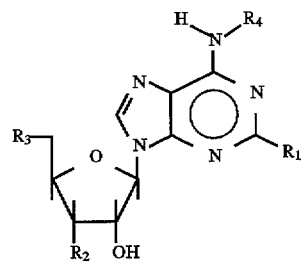

wherein:
$R_1$=H or $CH_3S$ and

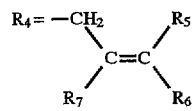

and
$R_5$=$CH_3$ or Cl
$R_6$=$CH_3$, $CH_2OH$ or Cl and
$R_1$=H or Br
or
$R_1$=H
and

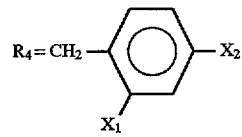

and $X_1$ and $X_2$ are independently selected from H, methyl, ethyl, hydroxy, the halogens and carboxyl

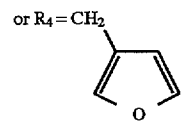

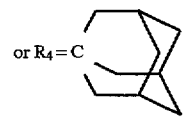

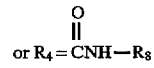

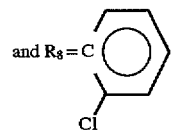

or
$R_8$=$(CH_2)_7CH_3$; and
$R_2$=OH and $R_3$=OH, monophosphate, diphosphate or triphosphate
or
$R_2$ and $R_3$ are linked to form a 3',5'-cyclic monophosphate derivative,
or a physiologically acceptable salt of any of the above. Listed below are the respective chemical groups $R_1$–$R_4$ for preferred compounds Ia–It according to the invention.

Ia: $R_1 = H$, $R_2 = OH$, $R_3 = OH$ and

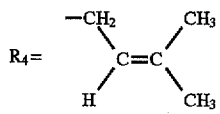

$N^6$-($\Delta^2$-isopentenyl) adenosine

Ib: $R_1 = H$, $R_2 = OH$, $R_3 =$ monophosphate, and

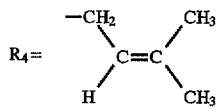

$N^6$-($\Delta^2$-isopentenyl) adenosine-5'-monophosphate

Ic: $R_1 = H$, $R_2$ and $R_3$ are linked to form a 3', 5'-cyclic monophosphate derivative, and

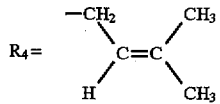

$N^6$-($\Delta^2$-isopentenyl) adenosine-3', 5'-cyclic monophosphate

Id: $R_1 = H$, $R_2 = OH$, $R_3 = OH$, and $R_4 = CH_2C_6H_5$
benzyladenosine

Ie: $R_1 = H$, $R_2 = OH$,
$R_3 =$ monophosphate, and $R_4 = CH_2C_6H_5$
$N^6$-benzyladenosine-5'-monophosphate If: $R_1 = H$, $R_2$ and $R_3$ are linked to form a 3',5'-cyclic monophosphate derivative and $R_4 = CH_2C_6H_5$
$N^6$-benzyladenosine-3',5'-cyclic monophosphate Ig: $R_1 = H$, $R_2 = OH$, $R_3 = OH$,

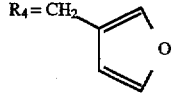

Furfuryladenosine

Ih: $R_1 = H$, $R_2 = OH$, $R_3 =$ monophosphate and

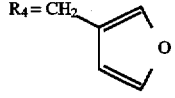

$N^6$-furfuryladenosine-5'-monophosphate

Ii: $R_1 = H$, $R_2$ and $R_3$ are linked to form a 3',5'-cyclic monophosphate derivative, and

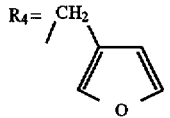

$N_6$-furfuryladenosine-3',5'-cyclic monophosphate

Ij: $R_1 = H$, $R_2 = OH$, $R_3 = OH$ and

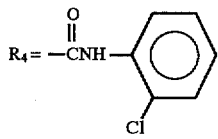

N-(purin-6-ylcarbamoyl)-o-chloroaniline ribonucleoside

Ik: $R_1 = H$, $R_2 = OH$, $R_3 =$ monophosphate and

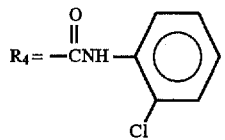

N-(purin-6-ylcarbamoyl)-o-chloroaniline ribonucleoside-5'-monophosphate

Il: $R_1 = H$, $R_2 = OH$, $R_3 = OH$ and

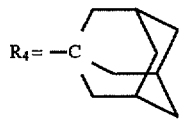

$N^6$-adamantyladenosine

Im: $R_1 = H$, $R_2 = OH$, $R_3 =$ monophosphate and

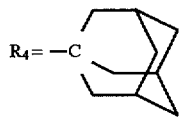

$N^6$-adamantyladenosine-5'-monophosphate

In: $R_1 = H$, $R_2 = OH$, $R_3 = OH$ and

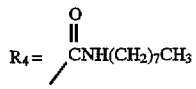

N-(purin-6-ylcarbamoyl)-n-octylamine ribonucleoside

Io: $R_1 = H$, $R_2 = OH$, $R_3 =$ monophosphate and

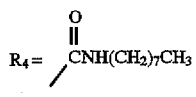

N-(purin-6-ylcarbamoyl)-n-octylamine ribonucleoside-5'-monophosphate

Ip: $R_1 = H$, $R_2$ and $R_3$ are linked to form a 3'-5'-cyclic monophosphate derivative, and

N-(purin-6-ylcarbamoyl)-n-octylamine ribonucleoside-3', 5'-cyclic monophosphate

Iq: $R_1 = CH_3S$, $R_2 = OH$, $R_3 = OH$, and $R_4 =$ 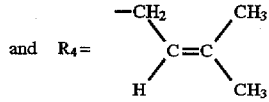

$N^6$-($\Delta^2$-isopentenyl)-2-methylthioadenosine

Ir: $R_1 = H$, $R_2 = OH$, $R_3 = OH$, and

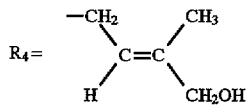

-continued

N⁶-(4-hydroxy-3-methyl-trans-2-butenyl) adenosine

Is: $R_1 = H$, $R_2 = OH$, $R_3 = OH$, and

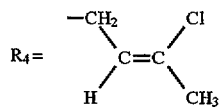

N⁶-(3-chloro-trans-2-butenyl) adenosine

It: $R_1 = H$, $R_2 = OH$, $R_3 = OH$, and

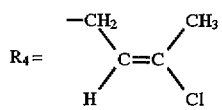

N⁶-(3-chloro-cis-2-butenyl) adenosine

The present invention also relates to a method of treatment of a patient, either animal or human, against viral infection, the treatment comprising administering an effective dosage of a pharmaceutical formulation, wherein the formulation comprises a compound selected from the group having the formula:

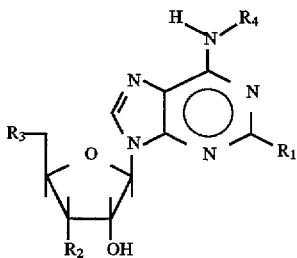

wherein:

$R_1$=H; $R_2$=CH$_3$; $R_3$=CH$_3$; and $R_4$=H, or wherein

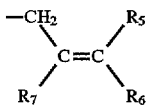

and $R_5$=CH$_3$ or Cl $R_6$=CH$_3$, CH$_2$OH or Cl and $R_7$=H or Br, $R_2$=OH and $R_3$=OH, monophosopate, diphosphate or triphosphate, or $R_2$ and $R_3$ are linked to form a 3',5'-cyclic monophosphate derivative.

Certain compounds of the family of compounds having formula I have been found in our in-vitro screen to have valuable pharmaceutical properties as anti-viral agents which were heretofore unknown.

For example, compound Ia, IPA, has been found through in-vitro experiments, described below, to inhibit the replication of HIV-1 in monocyte/macrophage cells and in T4 lymphocytes as well as Langerhan cells at levels which are non-toxic to the cells themselves.

Studies have been carried out which show that IPA reduces levels of HIV in HIV-infected macrophage cells treated with IPA relative to infected macrophage cells not treated with IPA. Toxicological studies have been carried out using uninfected cells (T and B lymphocytes and monocytes) which show that such cells can tolerate exposure in-vitro to IPA at levels which reduce levels of HIV in HIV-infected macrophage cells.

Studies have been carried out which indicate that IPA reduces in-vitro levels of HIV in HIV-infected H9, 81-66-45, and monocyte/macrophage cells relative to similar cells HIV-infected not treated with IPA.

Experiments to show the in-vitro effect of IPA on human leukocyte viability have been carried out.

Studies have been carried out that indicate that IPA, in in-vitro experiments, reduces levels of caprine arthritis encephalitis virus (CAEV) in Himalayan Tahr ovary cells.

Studies have been carried out which show that IPA reduces in-vitro levels of herpes simplex type 1 (HSV-1) in an M413 cell line of human fibroblasts.

Studies have been carried out which show that IPA reduces levels of cytomgelovirus in cells in-vitro.

Studies have been carried out which show that IPA reduces levels of Epstein-Barr Virus (EBV) in P$_3$HR1 cells in-vitro.

Compounds used according to this invention are administered as treatments against HIV by any suitable route including enteral, parenteral, topical, oral, rectal, nasal or vaginal routes. Parenteral routes include subcutaneous, intramuscular, intravenous and sublingual administration. Topical routes include buccal and sublingual administration. The preferred route of administration would be an intravenous one but oral administration of compounds having formula I would be the second preferred route.

The present invention further provides use of any compound of formula I in the manufacture or preparation of formulations, and especially pharmaceutical formulations, for use in treatments against HIV. The invention also provides the pharmaceutical formulations themselves.

The present invention further provides use of any compound of formula I combined with an adenosine deaminase inhibitor such as pentostatin to extend the half life of formula I compounds in the blood stream.

Pharmaceutical preparations prepared according to the invention include the compound of formula I contained in a gelatine capsule, in tablet form, dragee, syrup, suspension, topical cream, suppository, injectable solution, or kits for the preparation of syrups, suspension, topical cream, suppository or injectable solution just prior to use. Also, compounds of formula I may be included in composites which facilitate its slow release into the blood stream, e.g., silicone disc, polymer beads.

Pharmaceutical preparations prepared according to the invention include the employment of compounds of formula I in admixture with conventional excipients, that is, pharmaceutically acceptable organic or inorganic carrier substances which do not deleteriously react with the compounds. Suitable pharmaceutically acceptable carriers include, but are not limited to water, salt solutions, alcohols, gum arabic, vegetable oils, gelatine, carbohydrates, magnesium stearate, talc, silicic acid, viscous paraffin, fatty acid mono- and di-glycerides, etc.

The preparative procedure may include the sterilisation of the pharmaceutical preparations. The compounds may be mixed with auxiliary agents such as lubricants, preservatives, stabilisers, salts for influencing osmotic pressure, etc., which do not react deleteriously with the compounds.

Compounds of formula Ia can be stored dry almost indefinitely if protected from light and stored at −75 C. IPA is photosensitive and deteriorates at room temperature, whether in a solid form or in aqueous or ethanolic solutions.

It was found in experiments that the breakdown rate of IPA is approximately 3% per month in a dark container at room temperature.

Methods of treatment within the scope of this invention also include the use of physiologically acceptable salts of compounds of formula I and include, for example, those derived from inorganic acids such as hydrochloric, sulphuric, phosphoric acid, etc., and organic sulphuric acids such as p-toluenesulphonic acid, methanesulphonic acid, etc., and organic carboxylic acids such as acetic, oxalic, succinic, tartaric, citric, malic, maleic acid, etc.

The dosage of any one or more of compounds having formula I which is effective in treatment against HIV will depend on many factors including the specific compound or combination of compounds being utilised, the mode of administration, and the organism being treated. Dosages of a particular compound or combinations of compounds, each belonging to that class defined by formula I, for a given host can be determined using conventional considerations; for example, by customary comparison of the differential activities of the subject compounds and of a known agent, that is, by means of an appropriate pharmacological protocol. Further, the effectiveness of a particular regimen can be monitored by following over time the presences of HIV in blood samples of an organism being treated. There are available commercially kits for the detection of HIV antigens. The use of one such kit for detecting the antigen of HIV-I was used as described in Example Ia of this invention. It will be possible to cause a reduction, over a period of about two months, in the level of detectable p24 antigen in the blood serum of a patient by means of administration of compounds of formula I. A better measure of the progression of the level of infection would be the percentage infected macrophage population. Monocytes/macrophage cells obtained from either the blood or the lung during a course of treatment with compounds of formula I will show a reduction in recoverable HIV antigen as the therapy progresses.

In one embodiment of the invention, a pharmaceutical formulation comprising a compound having formula I is administered at the rate of 1 unit dose to 10 unit doses per day, and preferably 1 unit dose to 4 unit doses per day. The doses are given for periods of up to twelve weeks and in certain cases may be given for the life of the patient or, depending on the patient's medical requirements, at less frequent intervals.

In one aspect of the invention, a unit dose comprises 0.01 to 5000 mg of a formulation comprised of a compound having formula I.

In one embodiment of the invention, the pharmaceutical formulation is administered orally in unit doses once per day when the compound is in a slow release form or up to eight unit doses per day when the compound is in its native form. Alternatively or additionally, the pharmaceutical formulation is administered intravenously in unit doses comprising a compound having formula I in the range of 0.3 mg to 80 mg per Kg of body weight.

In one embodiment of the invention, a pharmaceutical formulation comprising a compound having formula I is administered by the use of a trans-dermal patch.

In one embodiment of the invention, a pharmaceutical formulation comprising a compound having formula I is administered using an emulsifying or semi-emulsifying formulation to improve absorption from the small intestine. Such an emulsion may be formulated using a derivative of coconut oil, eg. Miglyol 812.

In a particular embodiment of the invention, the method for treating a viral infection also includes treating a patient simultaneously with a pharmaceutical formulation comprising the compound dehydroepiandrosterone and/or its analogues. Alternatively, the pharmaceutical formulation comprises the method of treatment, in combination with any compound of formula I, dehydroepiandrosterone and/or its analogues or Etiocholanolone.

In another embodiment of the invention, the method of the invention comprises the step of treating a patient with known immune system booster or immune system modulator to enhance the production of T-cells by the bone marrow. The patient is treated with the immune system booster prior to administration of a pharmaceutical formulation comprising a compound having formula I. In another case, the patient is treated with the immune system booster until the level of production of T-cells by the bone marrow (having been reduced by the infection) is stabilised or begins to increase. In particular, the immune system booster is administered until the level of T-4 cells is stabilised or begins to increase.

In another embodiment of the invention, the method includes the step of treating a patient with an immune system booster both prior to and simultaneously while a pharmaceutical formulation comprising a compound having formula I is being administered.

EXAMPLES

Figure 1:
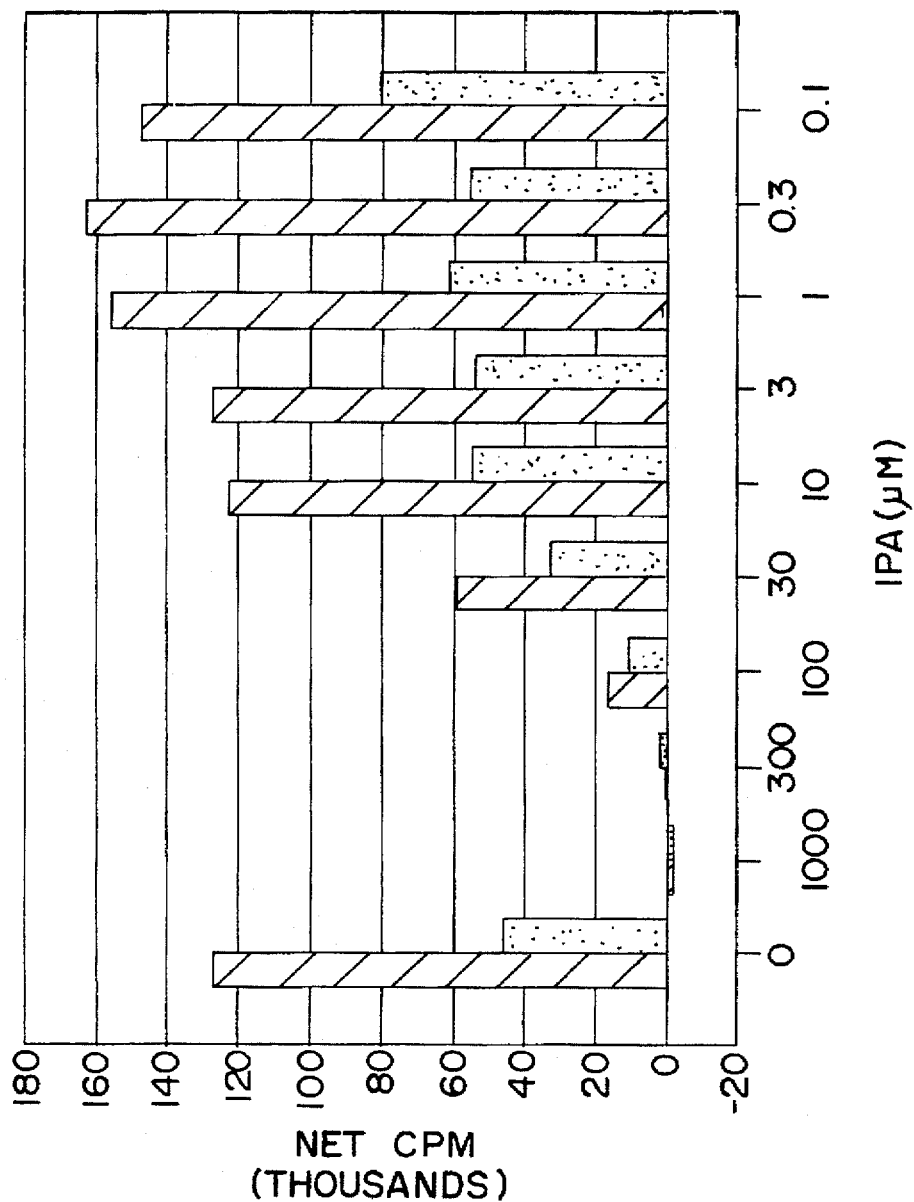
FIG. 1 is a graph of counts per minute versus concentration of IPA in an assay.

Tests were carried out to determine the effectiveness of IPA at reducing the levels of HIV-I in infected macrophages. Tests were also carried out to determine the toxicological effect of IPA on uninfected T lymphocytes, B lymphocytes and monocytes.

Experiments, described in the examples below, were carried out which show the effectiveness of IPA at reducing the levels of HIV-I in HIV-I-infected macrophage cells in-vitro. Experiments performed also show the relative effectiveness of AZT and dideoxycytidine (ddC) at reducing the levels of HIV-I in infected macrophage cells. Further experiments were carried out which show that human T and B lymphocytes and monocytes have a high tolerance for IPA in-vitro.

Generally, in experiments to test the ability of IPA to reduce the concentration of viral antigen, IPA was initially made into a 10 millimolar (mM) stock solution in sterile saline. This was used to produce final concentrations from 1 mM to 1 µM. Because IPA does not readily dissolve in water and is photosensitive, it was, in some case, dissolved at 2 mM directly into the growth medium, and this was used to make solutions of the desired concentrations.

EXPERIMENT Ia(a)

Macrophage Cells, HIV-I, Antibody Assay

Fresh macrophage cultures were obtained by incubation of mononuclear cells obtained from a leukopak directly in the wells of a microtiter plate having 6 wells per row. After removal of non-adherent cells, each row of the adherent macrophages was infected with 10-fold serial dilutions of HIV-I, with the use of polybrene to enhance uptake of the virus. After one to two hours, the virus inoculum was removed and replaced with fresh normal growth medium. The fresh medium for each row contained a particular concentration of AZT, dideoxy cytidine (ddC), or compound Ia, as indicated by the left-hand column of Table Ia(a). The first row of wells acted as a control, and to it was added fresh medium containing none of the three drugs. Medium levels were maintained for two to four weeks to allow replication of the virus to take place, with at least one complete fluid change to remove residual virus inoculum. The contents of each well were then tested for the level of HIV p24 antigen present using a commercially available antigen capture kit employing a radio-immunoassay which can detect as little as 10–9 gm of p24 present in a sample. The above procedure was done in duplicate runs.

The results were interpreted as follows: 2/2, for example, means that both the corresponding wells of both runs were positive for HIV-I p24, while 0/2 means that neither well was positive. The titers are given in the next to last column; where ½ wells was positive, an intermediate value was given to the titer that is half way between the two dilutions when calculated on a logarithmic scale. 3 µM IPA was positive in both wells at a dilution of 1/10,000 and in neither well at 1/100,000. Thus, one half log interval between $10^4$ and $10^5$ is $10^{4.5}$, or 30,000.

TABLE Ia(a)

| DRUG | | LOG VIRUS DILUTION | | | | | | TITER | PERCENT OF CONTROL |
|------|---|---|---|---|---|---|---|---|---|
| | | −1 | −2 | −3 | −4 | −5 | −6 | | |
| None | (control) | 2/2 | 2/2 | 2/2 | 2/2 | 1/2 | 0/2 | 100000 | 100 |
| ddC | 100 µM | 2/2 | 2/2 | 2/2 | 0/2 | 0/2 | 0/2 | 3000 | 3 |
| ddC | 10 µM | 2/2 | 2/2 | 2/2 | 1/2 | 0/2 | 0/2 | 10000 | 10 |
| IPA | 1000 µM | 0/2 | 0/2 | 0/2 | 0/2 | 0/2 | 0/2 | 10 | 0 |
| IPA | 300 µM | 0/2 | 0/2 | 0/2 | 0/2 | 0/2 | 0/2 | 10 | 0 |
| IPA | 100 µM | 2/2 | 2/2 | 0/2 | 0/2 | 0/2 | 0/2 | 300 | 0.3 |
| IPA | 30 µM | 2/2 | 2/2 | 1/2 | 0/2 | 0/2 | 0/2 | 1000 | 1 |
| IPA | 10 µM | 2/2 | 2/2 | 2/2 | 1/2 | 0/2 | 0/2 | 10000 | 10 |
| IPA | 3 µM | 2/2 | 2/2 | 2/2 | 2/2 | 0/2 | 0/2 | 30000 | 30 |

It was observed during these experiments that, although the monocyte/macrophage cultures appeared to be healthy at all concentrations of IPA used, the differentiation of small immature monocytes into large adherent macrophage cells did not take place in the presence of IPA.

EXPERIMENT Ia (b)

H9(Cells, HIV-1 Antibody Assay,

A procedure similar to that followed in Experiment Ia(a) followed using infected H9 cells, H9 cells being a permanent human T-cell line. The results are listed in Table Ia(b).

TABLE Ia(b)

| DRUG | CONCENTRATION | TITER | PERCENT INHIBITION |
|------|---------------|-------|---------------------|
| None | — | $1 \times 10^4$ | — |
| IPA | 1000 µM | <10 | >99.9 |
| IPA | 300 µM | <10 | >99.9 |
| IPA | 100 µM | 10 | 99.9 |
| IPA | 30 µM | $1 \times 10^2$ | 99 |
| IPA | 10 µM | $1 \times 10^3$ | 90 |
| IPA | 3 µM | $1 \times 10^3$ | 90 |
| IPA | 1 µM | $1 \times 10^4$ | 0 |
| ddC | 100 µM | 10 | 99.9 |
| ddC | 10 µM | $1 \times 10$ | 99 |

EXPERIMENT Ia(b)

H9 cells, HIV-I, Antibody Assay

A procedure similar to that followed in Experiment Ia(a) was followed using infected H9 cells, being a permanent human T-cell line. The results are listed in Table Ia(b) (i).

TABLE Ia(b)(i)

| DRUG | CONCENTRATION | TITER | PERCENT INHIBITION |
|------|---------------|-------|---------------------|
| None | — | $1 \times 10^4$ | — |
| IPA | 1000 µM | <10 | >99.9 |
| IPA | 300 µM | <10 | >99.9 |
| IPA | 100 µM | 10 | 99.9 |
| IPA | 30 µM | $1 \times 10^2$ | 99 |
| IPA | 10 µM | $3 \times 10^3$ | 90 |
| IPA | 3 µM | $1 \times 10^3$ | 90 |
| IPA | 1 µM | $1 \times 10^4$ | 0 |
| ddC | 100 µM | 10 | 99.9 |
| ddC | 10 µM | $1 \times 10$ | 99 |

These experiments were repeated and the results are listed in Table Ia(b) (ii).

TABLE Ia(b)(ii)

| DRUG | CONCENTRATION | TITER | PERCENT INHIBITION |
|---|---|---|---|
| None | — | $1 \times 10^4$ | — |
| IPA | 1000 µM | <10 | >99.9 |
| IPA | 300 µM | <10 | >99.9 |
| IPA | 100 µM | <10 | >99.9 |
| IPA | 30 µM | <10 | >99.9 |
| IPA | 10 µM | $3 \times 10^2$ | 97 |
| IPA | 3 µM | $1 \times 10^4$ | 0 |
| IPA | 1 µM | $1 \times 10^4$ | 0 |
| AZT | 100 µM | <10 | >99.9 |
| AZT | 10 µM | <10 | >99.9 |
| ddC | 100 µM | <10 | >99.9 |
| ddC | 10 µM | <10 | >99.9 |

EXPERIMENT Ia (c)

Himalayan Tahr Ovary Cells, CAEV, Antibody Assay

A procedure similar to that followed in Experiment Ia (a) was followed using Himalayan Tahr ovary cells exposed to caprine arthritis encephalitis virus (CAEV), a lentivirus related to HIV-1 which causes leukoencephalitis and arthritis in goats. A radioimmunoassay to detect CAEV p28 was used to determine the presence of the virus. Results are listed in Table Ia (c).

TABLE Ia(c)

| DRUG | \-1 | \-2 | \-3 | \-4 | \-5 | \-6 | TITER | PERCENT INHIBITION |
|---|---|---|---|---|---|---|---|---|
| | | | LOG VIRUS DILUTION | | | | | |
| None | 2/2 | 2/2 | 2/2 | 1/2 | 0/2 | 0/2 | $3 \times 10^8$ | 0 |
| IPA 300 µM | 2/2 | 2/2 | 2/2 | 2/2 | 1/2 | 0/2 | $3 \times 10^6$ | 99 |
| IPA 100 µM | 2/2 | 2/2 | 2/2 | 1/2 | 0/2 | 0/2 | $3 \times 10^6$ | 99 |
| IPA 30 µM | 2/2 | 2/2 | 2/2 | 2/2 | 1/2 | 0/2 | $3 \times 10^7$ | 90 |
| IPA 10 µM | 2/2 | 2/2 | 2/2 | 0/2 | 0/2 | 0/2 | $1 \times 10^8$ | 67 |
| IPA 3 µM | 2/2 | 2/2 | 2/2 | 1/2 | 0/2 | 0/2 | $3 \times 10^8$ | 0 |
| IPA 1 µM | 2/2 | 2/2 | 2/2 | 1/2 | 0/2 | 0/2 | $3 \times 10^8$ | 0 |
| AZT 100 µM | 0/2 | 0/2 | 0/2 | 0/2 | 0/2 | 0/2 | $1 \times 10^8$ | 67 |
| AZT 10 µM | 0/2 | 0/2 | 0/2 | 0/2 | 0/2 | 0/2 | $3 \times 10^8$ | 0 |
| ddC 100 µM | 2/2 | 0/2 | 0/2 | 0/2 | 0/2 | 0/2 | <$1 \times 10$ | 99.99 |
| ddC 10 µM | 2/2 | 1/2 | 0/2 | 0/2 | 0/2 | 0/2 | $3 \times 10^4$ | 99.99 |

EXPERIMENT Ia(d)

Effects of IPA, AZT and ddC on Human Cell Viability

Human peripheral blood mononuclear cells were incubated for 18 hours in the presence of various concentrations of IPA and azidothymidine (AZT) at 370° C. after which time cell viability was determined by visual counts of cells in the presence of trypan blue. The results are tabulated in Table Ia(d) (i). Two controls were run, one with each series of experiments. No toxicity was observed for AZT concentrations between 0.1 µM and 6 mM. There was a slight reduction in cell viability in the presence of 6 mM IPA, but no toxic effect was observed using concentrations of from 0.1 µM to 3 mM.

TABLE Ia(d)(i)

| | AZT 18 Hours | | IPA 18 Hours | |
|---|---|---|---|---|
| Concentration (µM) | Cells/ml ($\times 10^5$) | Viability (%) | Cells/ml ($\times 10^5$) | Viability (%) |
| 6000 | 3.8 | 95 | 2.4 | 75 |
| 3000 | 3.0 | 88 | 2.2 | 92 |
| 1000 | 2.2 | 100 | 2.8 | 82 |
| 300 | 2.4 | 92 | 2.2 | 79 |
| 100 | 2.0 | 91 | 3.8 | 90 |
| 30 | 3.0 | 100 | 3.8 | 95 |
| 10 | 1.8 | 90 | 3.0 | 94 |
| 3 | 2.0 | 100 | 2.6 | 87 |
| 1 | 1.8 | 90 | 2.8 | 100 |
| 0.3 | 2.0 | 91 | 1.8 | 82 |
| 0.1 | 3.4 | 100 | 2.4 | 86 |
| control | 3.2 | 94 | 2.6 | 87 |

Experiments were also performed to determine the toxic effect of IPA, AZT and ddC on other cell lines. The results are tabulated in Tables Ia(d) (ii) to Ia(d) (v).

Two lots of IPA (Sample 1 and Sample 2) were tested. Tests of Sample 1 over four months indicated there was no change in the compound.

TABLE Ia(d)(ii)

CELL LINE: H9, Continuous Exposure for 10 days

| DRUG | CONCENTRATION (µM) | PERCENT VIABLE CELLS |
|---|---|---|
| AZT | 100 | 61 |
| AZT | 10 | 77 |
| AZT | 1 | 83 |
| ddC | 100 | 68 |
| ddC | 10 | 79 |
| ddC | 1 | 93 |
| Sample 1 | | |
| IPA | 1000 | 12 |
| IPA | 300 | 18 |
| IPA | 100 | 20 |
| IPA | 30 | 56 |
| IPA | 10 | 73 |
| IPA | 3 | 84 |
| IPA | 1 | 86 |
| Sample 2 | | |
| IPA | 1000 | 7 |
| IPA | 300 | 21 |
| IPA | 100 | 23 |
| IPA | 30 | 61 |
| IPA | 10 | 78 |
| IPA | 3 | 81 |
| IPA | 1 | 84 |
| CONTROL | | 87 |

TABLE Ia(d)(iii)

CELL LINE: H9, HIV Chronically Infected, Continuous Exposure for 4 days

| DRUG | CONCENTRATION (µM) | PERCENT VIABLE CELLS |
|---|---|---|
| AZT | 100 | 76 |
| AZT | 10 | 81 |
| AZT | 1 | 88 |
| ddC | 100 | 68 |
| ddC | 10 | 79 |
| ddC | 1 | 91 |

TABLE Ia(d)(iii)-continued

CELL LINE: H9, HIV Chronically Infected, Continuous Exposure for 4 days

| DRUG | CONCENTRATION (μM) | PERCENT VIABLE CELLS |
| --- | --- | --- |
| Sample 1 | | |
| IPA | 1000 | 51 |
| IPA | 300 | 48 |
| IPA | 100 | 60 |
| IPA | 30 | 73 |
| IPA | 10 | 85 |
| IPA | 3 | 89 |
| IPA | 1 | 93 |
| Sample 2 | | |
| IPA | 1000 | 57 |
| IPA | 300 | 53 |
| IPA | 100 | 66 |
| IPA | 30 | 78 |
| IPA | 10 | 86 |
| IPA | 3 | 89 |
| IPA | 1 | 92 |
| CONTROL | | 91 |

TABLE Ia(d)(iv)

CELL LINE 81-66-45

DAYS EXPOSED TO DRUG (PERCENT VIABLE CELLS)

| TYPE OR EXPOSURE | CONC (μM) | 1 DAY | 4 DAYS, CONT. | 10 DAYS, CONT. | 4 DAYS, 1 DAY EXP | 10 DAYS, 1 DAY EXP |
| --- | --- | --- | --- | --- | --- | --- |
| AZT | 100 | 95 | 78 | 56 | 76 | 64 |
| AZT | 10 | 95 | 74 | 68 | 85 | 70 |
| AZT | 1 | 93 | 80 | 75 | 85 | 79 |
| ddC | 100 | 92 | 66 | 53 | 93 | 58 |
| ddC | 10 | 90 | 78 | 71 | 85 | 75 |
| ddC | 1 | 95 | 63 | 82 | 77 | 79 |
| IPA | 1000 | 58 | 52 | 18 | 73 | 38 |
| IPA | 300 | 74 | 65 | 26 | 72 | 51 |
| IPA | 100 | 66 | 60 | 34 | 84 | 59 |
| IPA | 30 | 62 | 56 | 44 | 92 | 68 |
| IPA | 10 | 81 | 85 | 70 | 84 | 79 |
| IPA | 3 | 75 | 85 | 78 | 90 | 88 |
| IPA | 1 | 80 | 84 | 81 | 89 | 81 |
| IPA | 1000 | 63 | 51 | 15 | 65 | 42 |
| IPA | 300 | 77 | 40 | 22 | 70 | 50 |
| IPA | 100 | 71 | 47 | 26 | 82 | 61 |
| IPA | 30 | 75 | 65 | 43 | 80 | 77 |
| IPA | 10 | 78 | 88 | 66 | 89 | 83 |
| IPA | 3 | 79 | 84 | 79 | 80 | 88 |
| IPA | 1 | 91 | 78 | 72 | 80 | 92 |
| CONTROL | N/A | 95 | 75 | 84 | 95 | 90 |

TABLE Ia(d)(v)

MONOCYTE/MACROPHAGE CELLS

| TYPE OR EXPOSURE DRUG | CONC (μM) | 1 DAY | 4 DAYS, CONT. | 10 DAYS, CONT. | 4 DAYS, 1 DAY EXP | 10 DAYS, 1 DAY EXP |
| --- | --- | --- | --- | --- | --- | --- |
| AZT | 100 | ++++ | ++++ | +++ | ++++ | +++ |
| AZT | 10 | ++++ | ++++ | ++++ | ++++ | ++++ |
| AZT | 1 | +++ | ++++ | ++++ | ++++ | ++++ |
| ddC | 100 | ++++ | ++++ | +++ | ++++ | +++ |
| ddC | 10 | +++ | ++++ | ++++ | ++++ | +++ |
| ddC | 1 | ++++ | ++++ | ++++ | ++++ | ++++ |
| IPA, OLD | 1000 | ++ | 0 | 0 | + | ++ |
| IPA, OLD | 300 | ++ | ++ | + | ++ | ++ |
| IPA, OLD | 100 | ++ | ++ | ++ | +++ | +++ |
| IPA, OLD | 30 | +++ | ++ | ++ | +++ | +++ |
| IPA, OLD | 10 | +++ | +++ | +++ | ++++ | ++++ |
| IPA, OLD | 3 | ++++ | +++ | ++ | ++++ | ++++ |
| IPA, OLD | 1 | ++++ | ++++ | ++++ | ++++ | ++++ |
| IPA, NEW | 1000 | ++ | 0 | 0 | + | ++ |
| IPA, NEW | 300 | ++ | ++ | + | ++ | ++ |
| IPA, NEW | 100 | ++ | ++ | ++ | +++ | +++ |
| IPA, NEW | 30 | +++ | ++ | ++ | +++ | +++ |
| IPA, NEW | 10 | +++ | +++ | +++ | ++++ | ++++ |
| IPA, NEW | 3 | ++++ | +++ | ++ | ++++ | ++++ |
| IPA, NEW | 1 | ++++ | ++++ | ++++ | ++++ | ++++ |
| CONTROL | N/A | ++++ | ++++ | ++++ | ++++ | ++++ |

Note: Since monocyte/macrophage cells are tightly adherant to the wells, they cannot be trypsinized to stain and count. We were also unable to effectively observe dye uptake directly in the well, so the observations made above represent qualitative indications of the apparent health of the cells as well as the cell numbers.

Nevertheless, it is important to note that these monocyte/macrophage cells appear to be far more resistant to the toxic effect of IPA than the T cell lines, for example. Since the tahr cells used for CAEV testing were also relatively resistant to IPA, it may be that the most rapidly growing cells are most vulnerable.

EXPERIMENT 1a(e)

Effects of Drugs on Human T and B Lymphocyte Function

Tests were carried out to determine the effect of compound Ia on normal human T and B lymphocyte functions.

T and B lymphocytes from normal human donors were incubated for 30 minutes at various dose levels of the compounds indicated. The lymphocytes were added in triplicate wells in gentamicin and phytohemagglutinin (PHA) (a T cell mitogen), pokeweed mitogen (PWM) (a B cell mitogen) and allogeneic mononuclear cells (mixed leukocyte cultures; MLC) or media containing the above additives. The lymphocyte blastogenesis assay is described in detail below.

The results of the various assays are summarised in Charts Ia(e) (i)–Ia(e) (xii) (FIGS. 1–12). Enhanced blastogenesis of cells was interpreted to indicate stimulation of cell activity.

Figure 2:
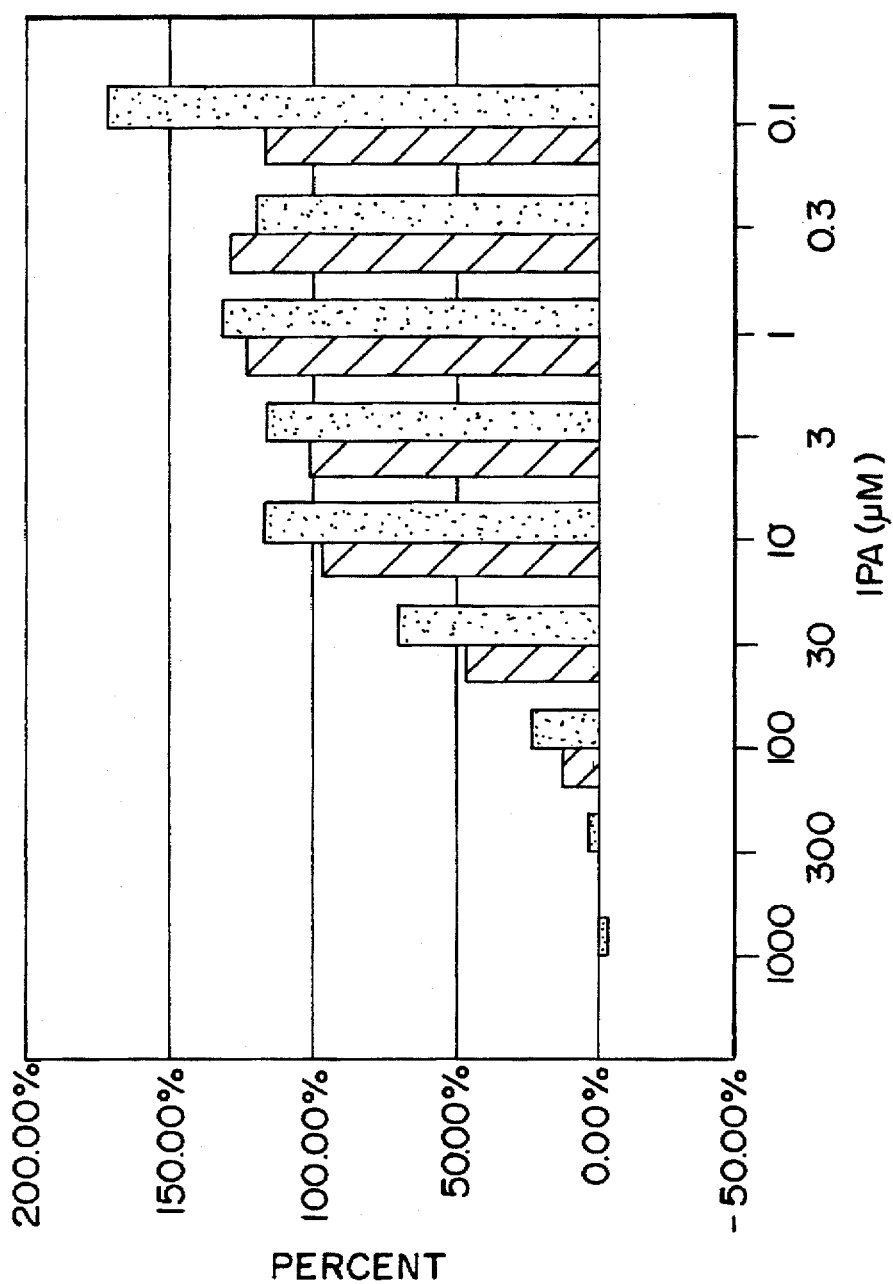
FIG. 2 is a graph of percentage increase or decrease in proliferation capability versus concentration of IPA in an assay.

The data are represented as the mean of the three replicates. The results are presented in Charts Ia(e) (i) and Ia(e) (ii) (FIGS. 1 and 2). Chart Ia(e) (i) (FIG. 1) presents the data as net counts per minute (CPM) (mean CPM in mitogen containing wells) and Chart Ia(e) (ii) (FIG. 2) shows a percentage increase or decrease (% change=(net CPM of wells with IPA/net CPM of wells with media)×100) in proliferation capability in cell cultures in which IPA was added as compared to cell cultures without IPA. A reduction of both T lymphocytes' abilities to proliferate was obtained when 100 μM or greater concentrations of IPA was added to the cell cultures. Proliferative activity of T lymphocytes by 25% at the 30 μM concentration of IPA in the experiment. No effect or an increase in T and B lymphocyte proliferation was observed when 0.1–10 μM concentrations of IPA were added to the cell cultures.

Figure 3:
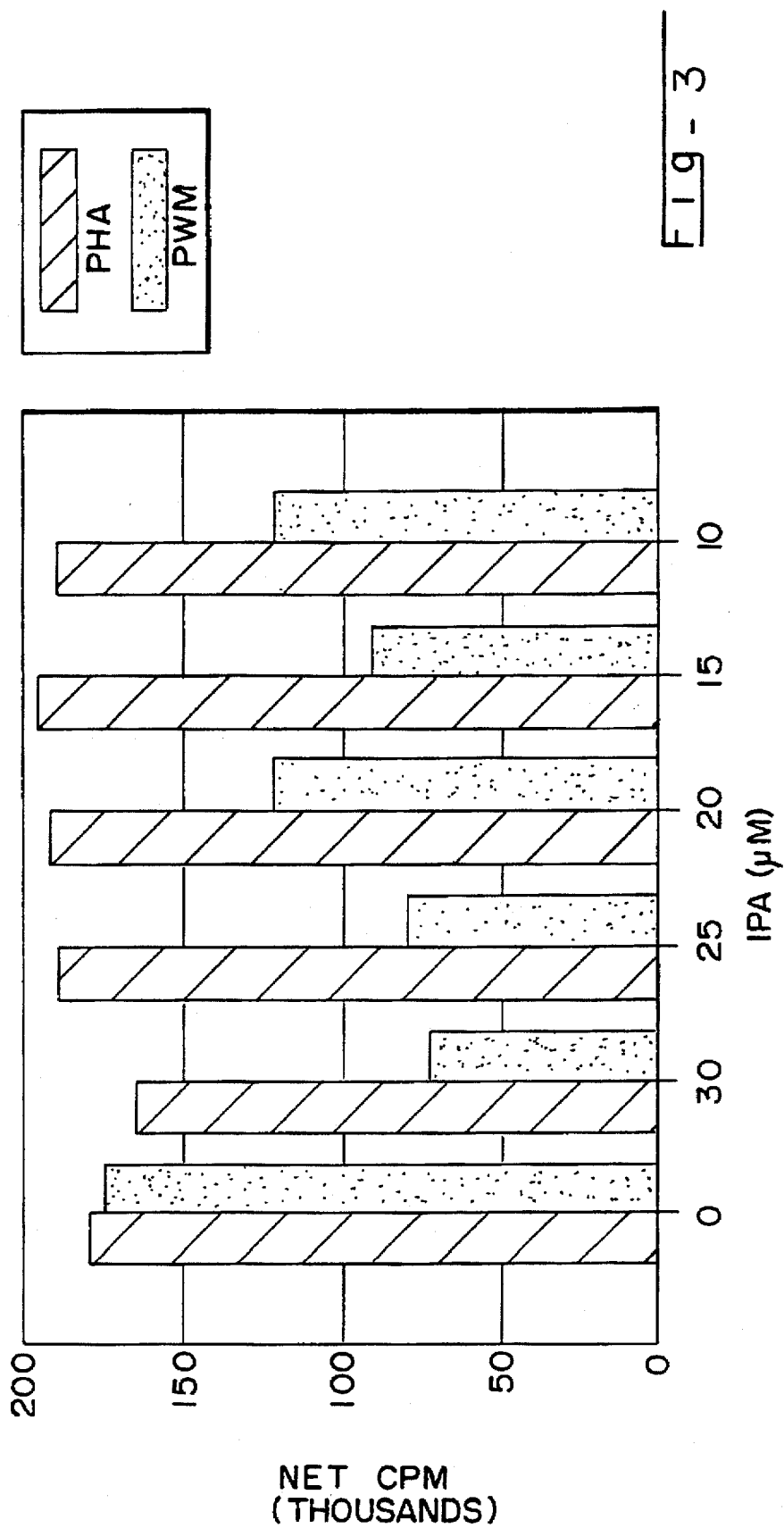
FIG. 3 is a graph of counts per minute versus concentration of IPA in an assay.
Figure 4:
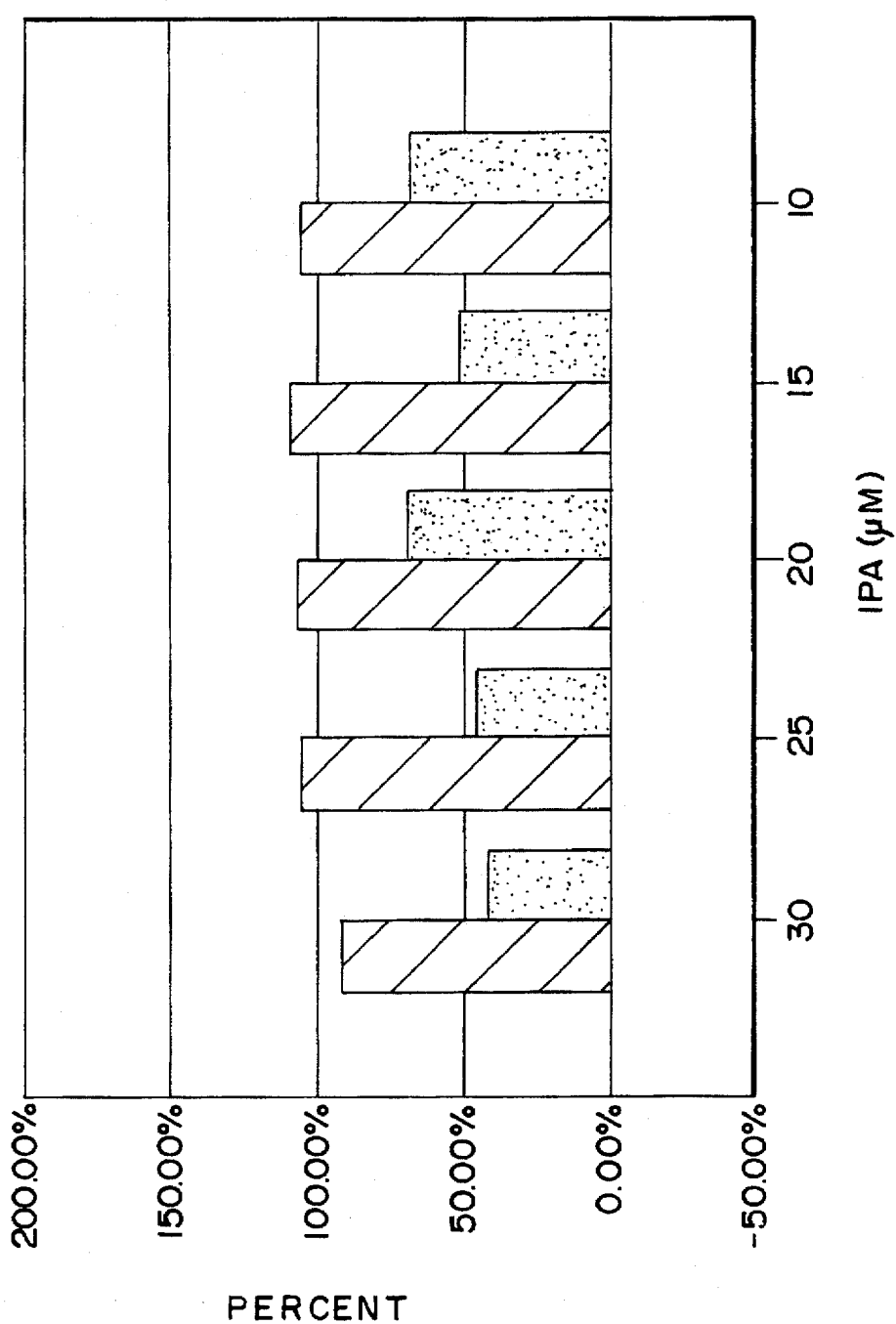
FIG. 4 is a graph of percentage increase or decrease of T and B lymphocyte proliferation versus concentration of IPA in an assay.

A second experiment was conducted where a more narrow dose level range of IPA was added to cell cultures and T and B lymphocyte proliferation was measured (Charts Ia(e) (iii) and Ia(e) (iv) (FIGS. 3 and 4). No appreciable reduction in T lymphocyte proliferation was observed with dose levels of IPA ranging from 30 down to 10 µM. An approximate reduction of B lymphocyte proliferation of 30–50% was observed between the 30–10 µM concentration levels. The degree of variation observed between experiments is common in these tests. (Luster, et al. Development of a Testing Battery To Assess Chemical—Induced Immunotoxicity: National Toxicology Program's Guidelines for Immunotoxicity Evaluation in Mice).

Figure 5:
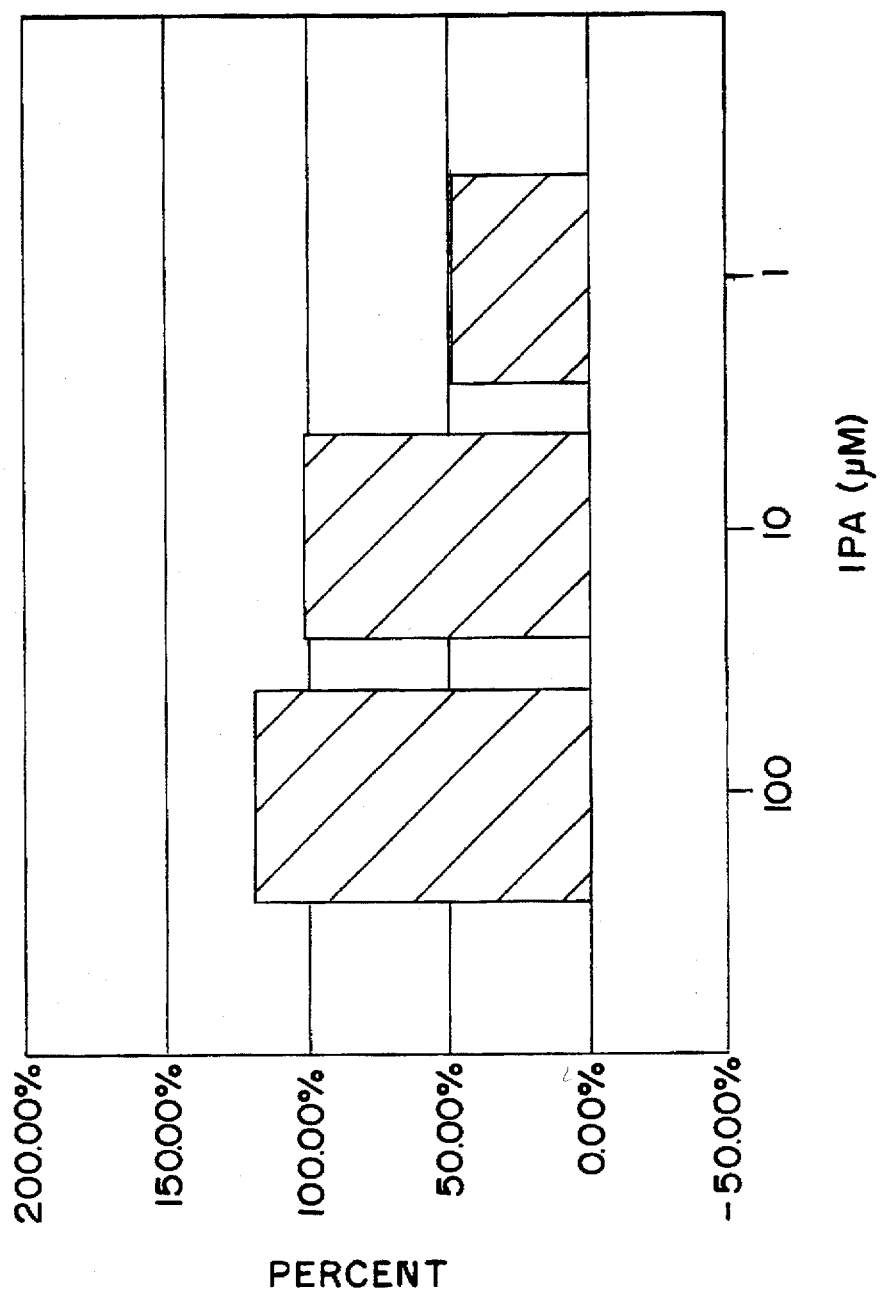
FIG. 5 is a graph of percentage increase or decrease of MLC reactivity versus concentration of IPA in an assay
Figure 6:
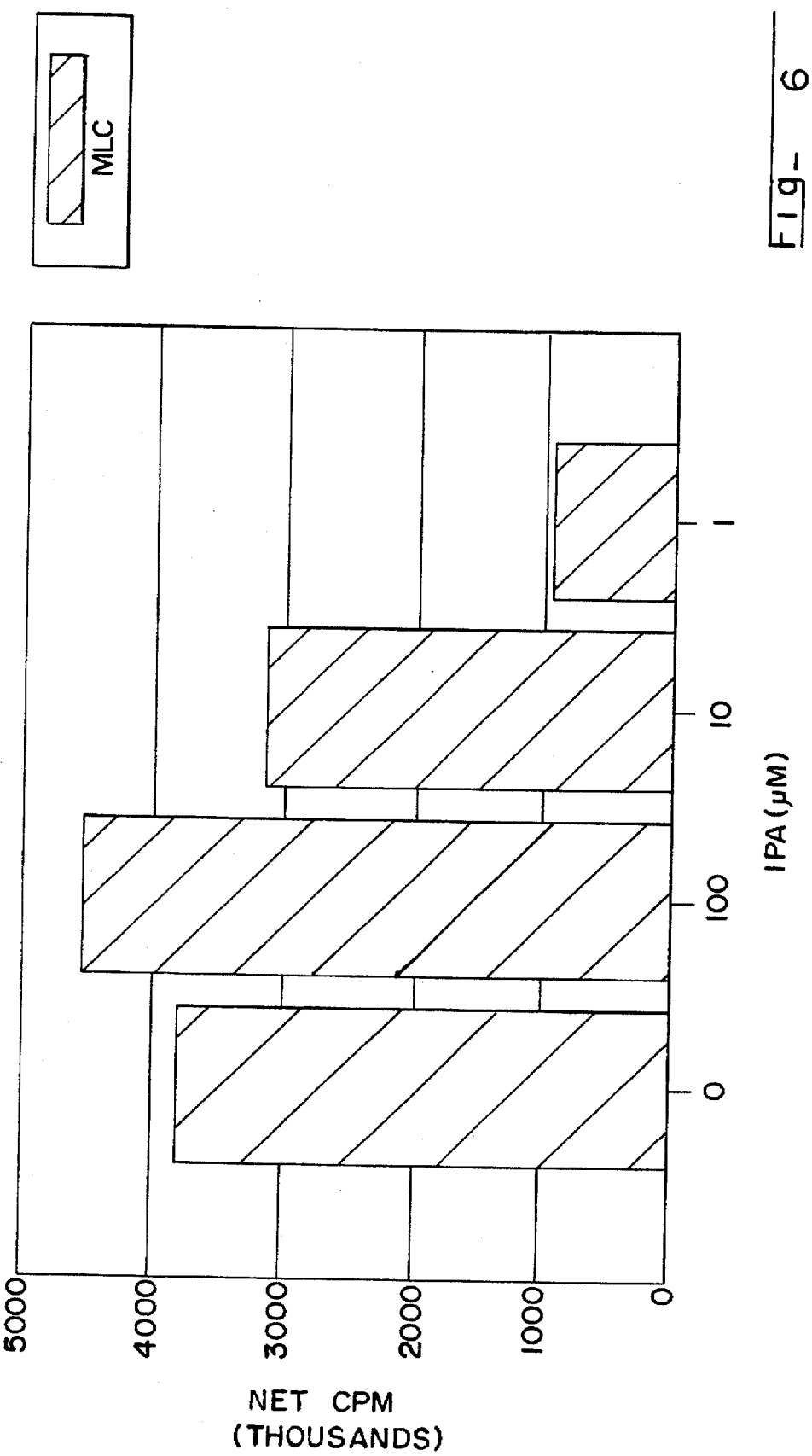
FIG. 6 is a graph of counts per minute versus concentration of IPA in an assay.

Mixed leukocyte culture (MLC) reactions may be used to evaluate the ability of human mononuclear cells to recognise and immunologically react to human histocompatibility antigen (measurement of the ability of the cells to mount a primary immune response to an antigen). Cultures of one set of human mononuclear cells were reacted with mononuclear cells from an unrelated donor in lymphocyte blastogenesis assays and the proliferation of the first set of cells was quantitated. The results are presented in Charts Ia(e) (v) and Ia(e) (vi) (FIGS. 5 and 6). Again, as with lymphocyte blastogenesis with mitogens, the MLC was run in replicates of three and a mean value obtained. A slight increase in MLC reactivity was seen when 100 µM of IPA were added to the cultures. No effect on MLC reactivity was seen with 10 µM of IPA and a 50% reduction in MLC reactivity was obtained at the 1 µM concentration.

Figure 7:
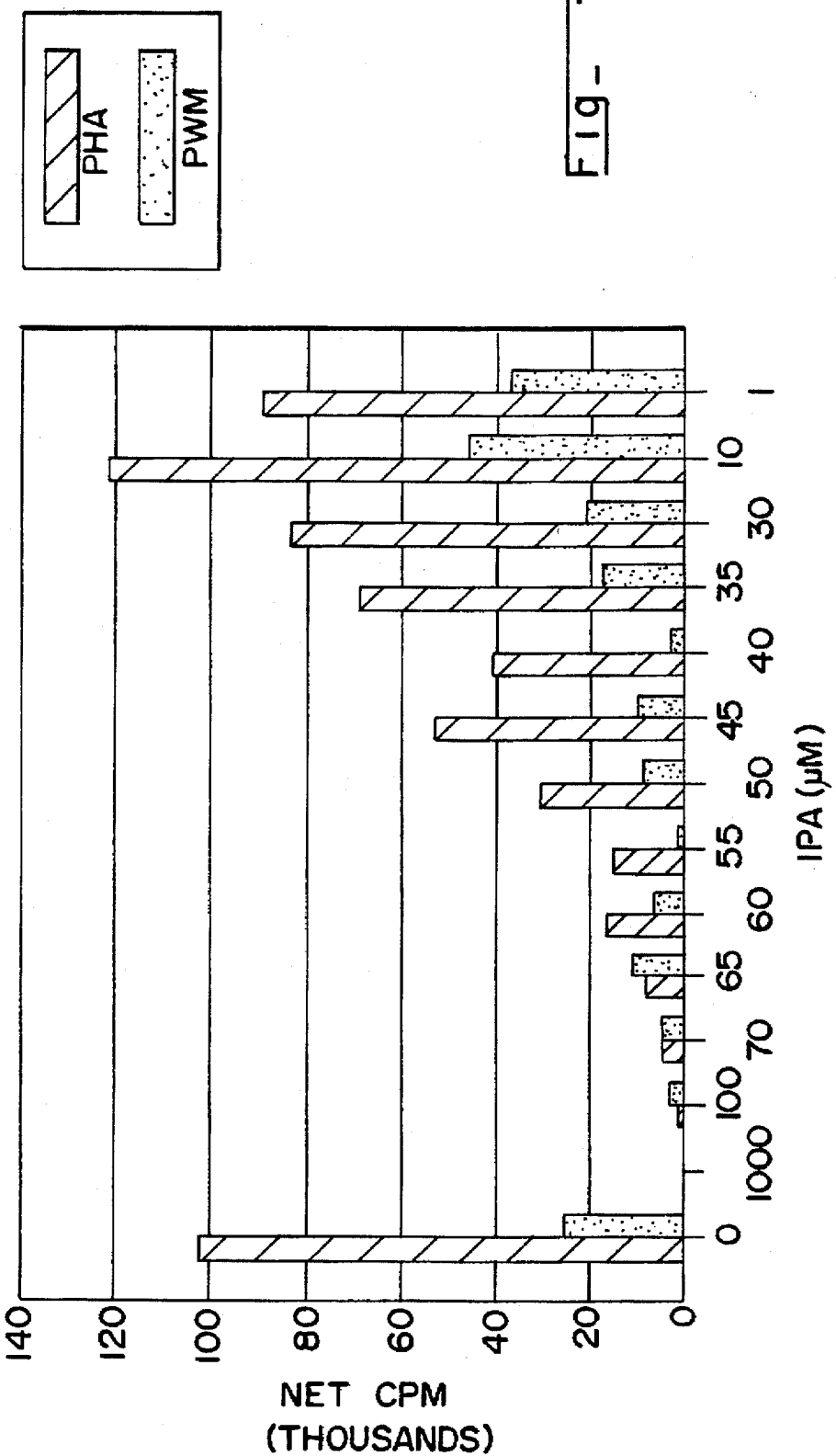
FIG. 7 is a graph of counts per minute versus concentration of IPA in an assay.
Figure 8:
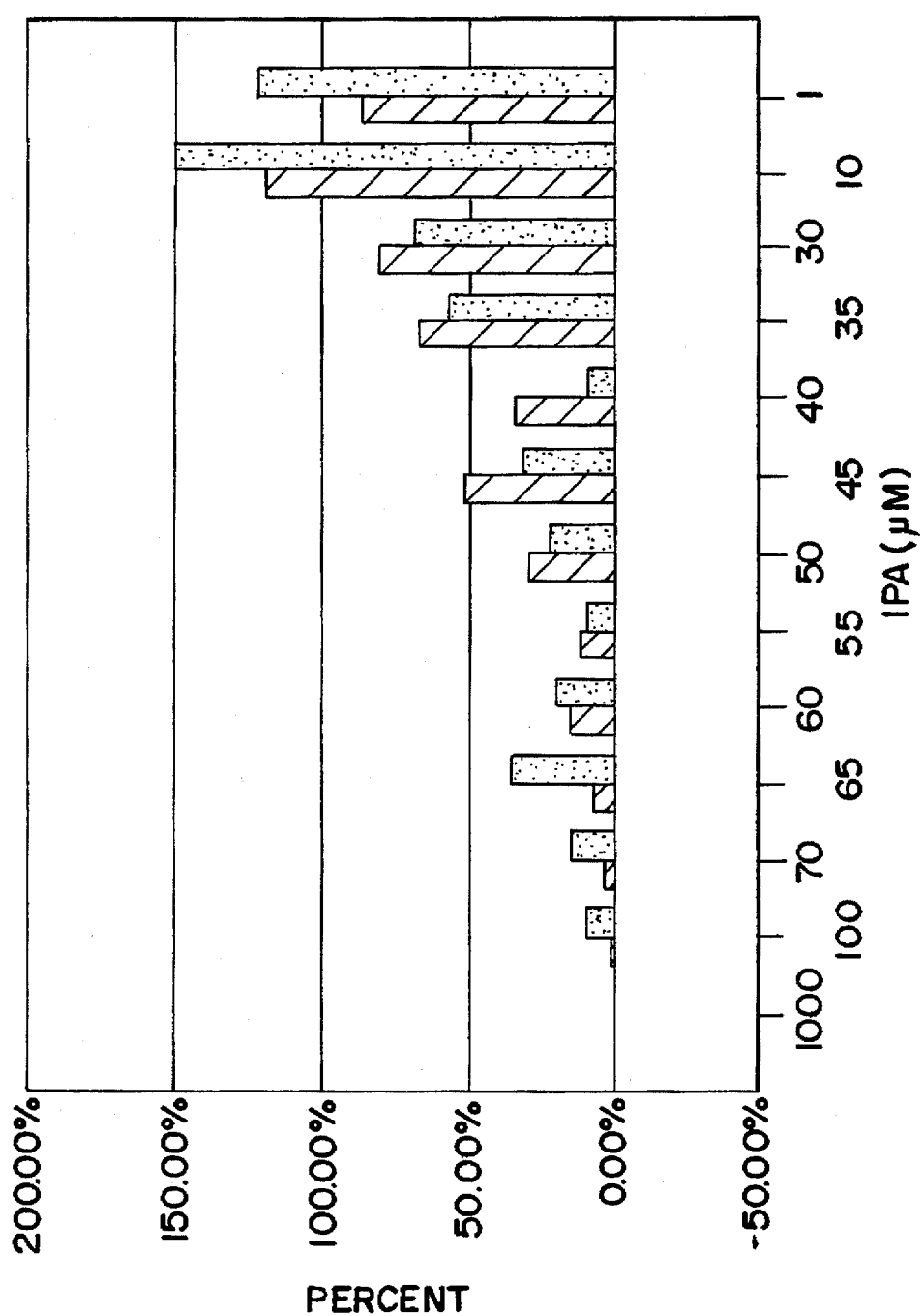
FIG. 8 is a graph of percentage increase or decrease of T and B lymphocyte function versus concentration of IPA in an assay.
Figure 9:
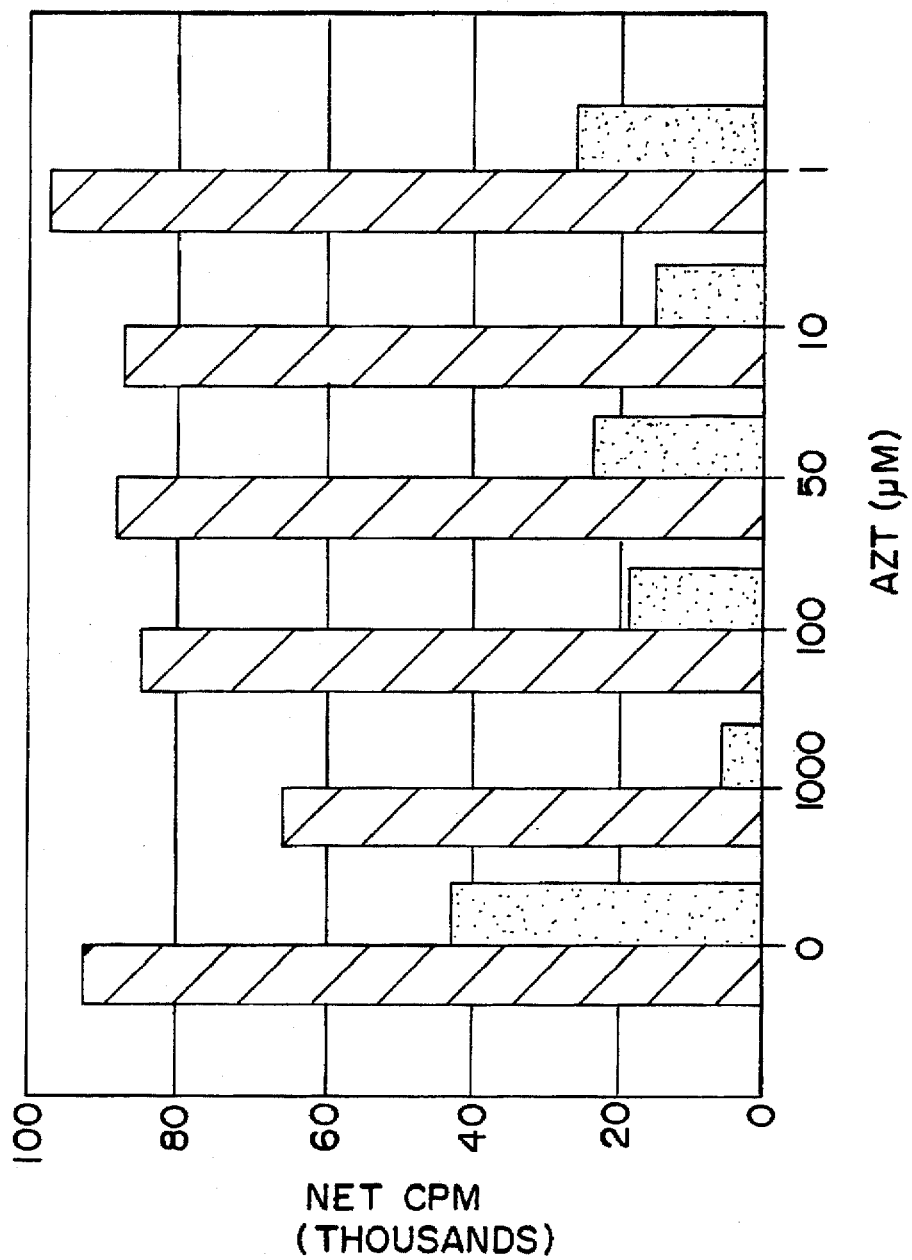
FIG. 9 and 10 are graphs of T lymphocyte proliferation versus concentration of AZT in an assay.
Figure 10:
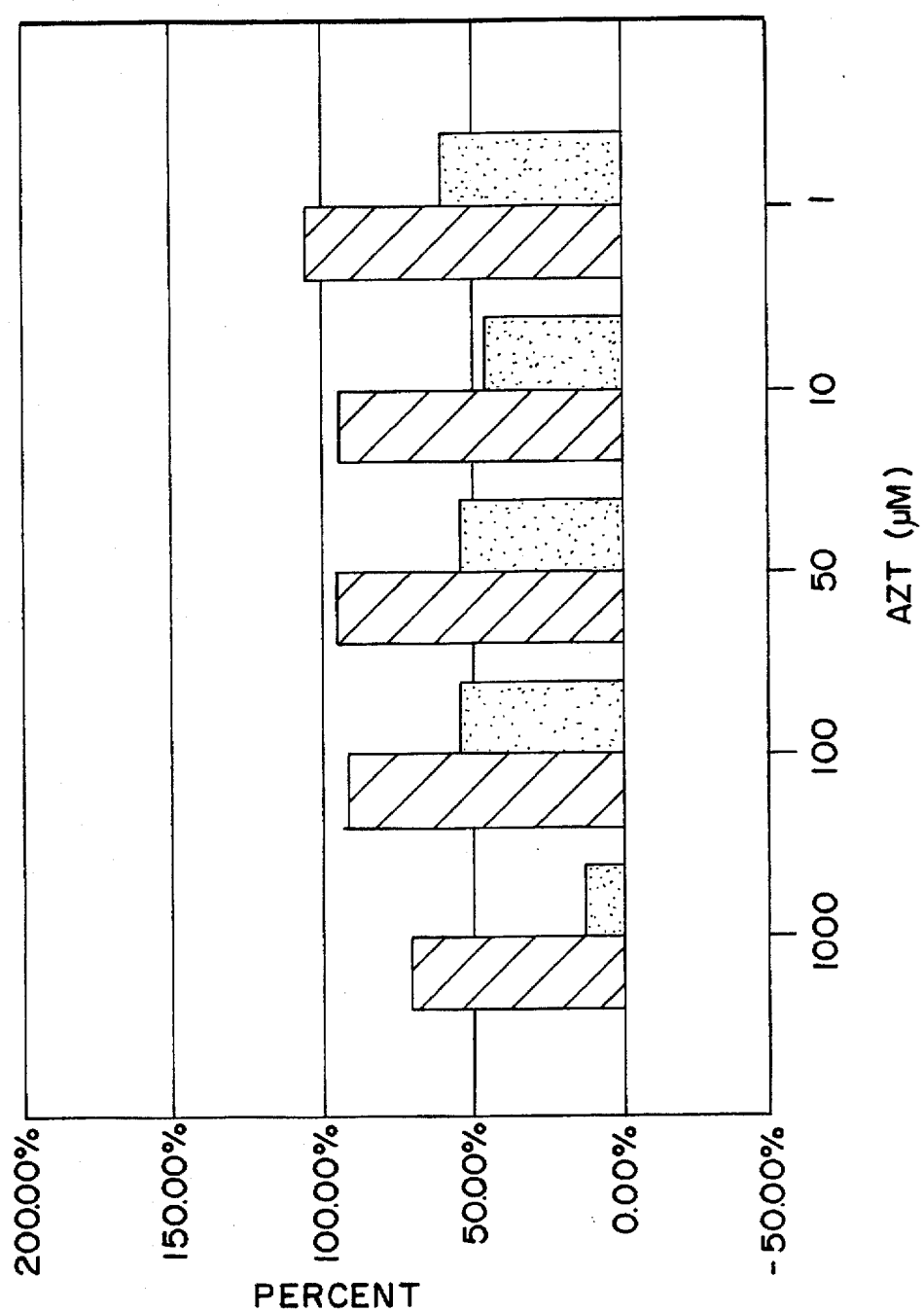

To more closely observe the "no effect" dose level of IPA on T and B lymphocyte function, an experiment was conducted where very close dose level intervals were run in lymphocyte blastogenesis assays. Within this experiment, the comparative effects of wide dose levels (1000–1 µM) of AZT and ddC were also evaluated on T and B lymphocyte function. The results are shown in Charts Ia(e) (vii)–Ia(e) (xii) (FIGS. 7–12). Again, reductions in T and B lymphocyte function were obtained with IPA at dose levels ranging from 1000 µM down to 10 µM. An approximate 25% reduction in both T and B lymphocyte function was seen at the 30–35 µM concentration of IPA (Charts Ia(e) (vii) and Ia(e) (viii) (FIGS. 7 and 8). Increased T and B lymphocyte responsiveness was observed at the 10 µM dose level.

No appreciable decrease in T lymphocyte proliferation was obtained at 100–1 µM concentrations of AZT (Charts Ia(e) (ix) and Ia(e) (x) (FIGS. 9 and 10 ); an approximate 25% reduction was seen at the 1000 µM dose level of AZT on T cells. AZT at all dose levels, 1000–1 µM, caused decreases in B lymphocyte proliferation (50–90%) reduction.

Figure 11:
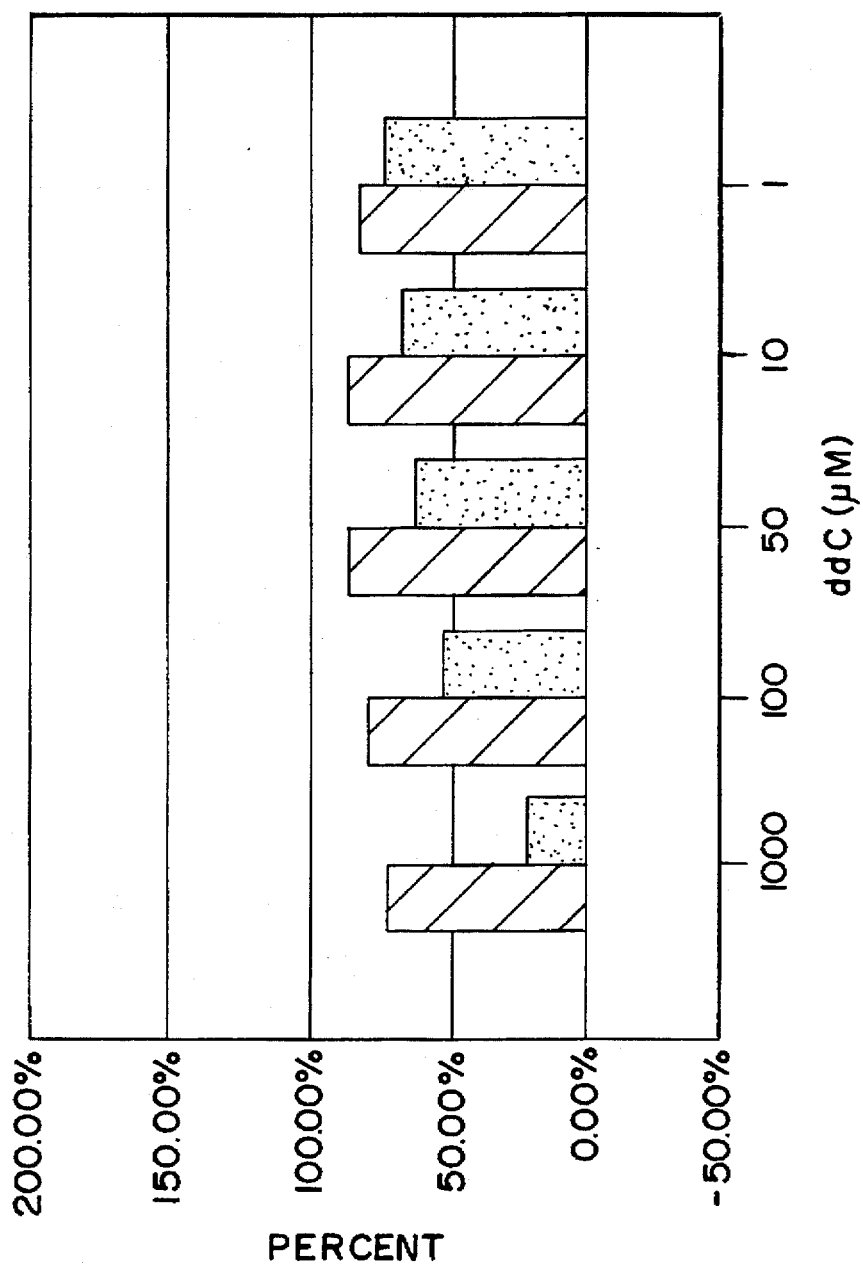
FIG. 11 and 12 are graphs of T lymphocyte function versus concentration of ddC in an assay.
Figure 12:
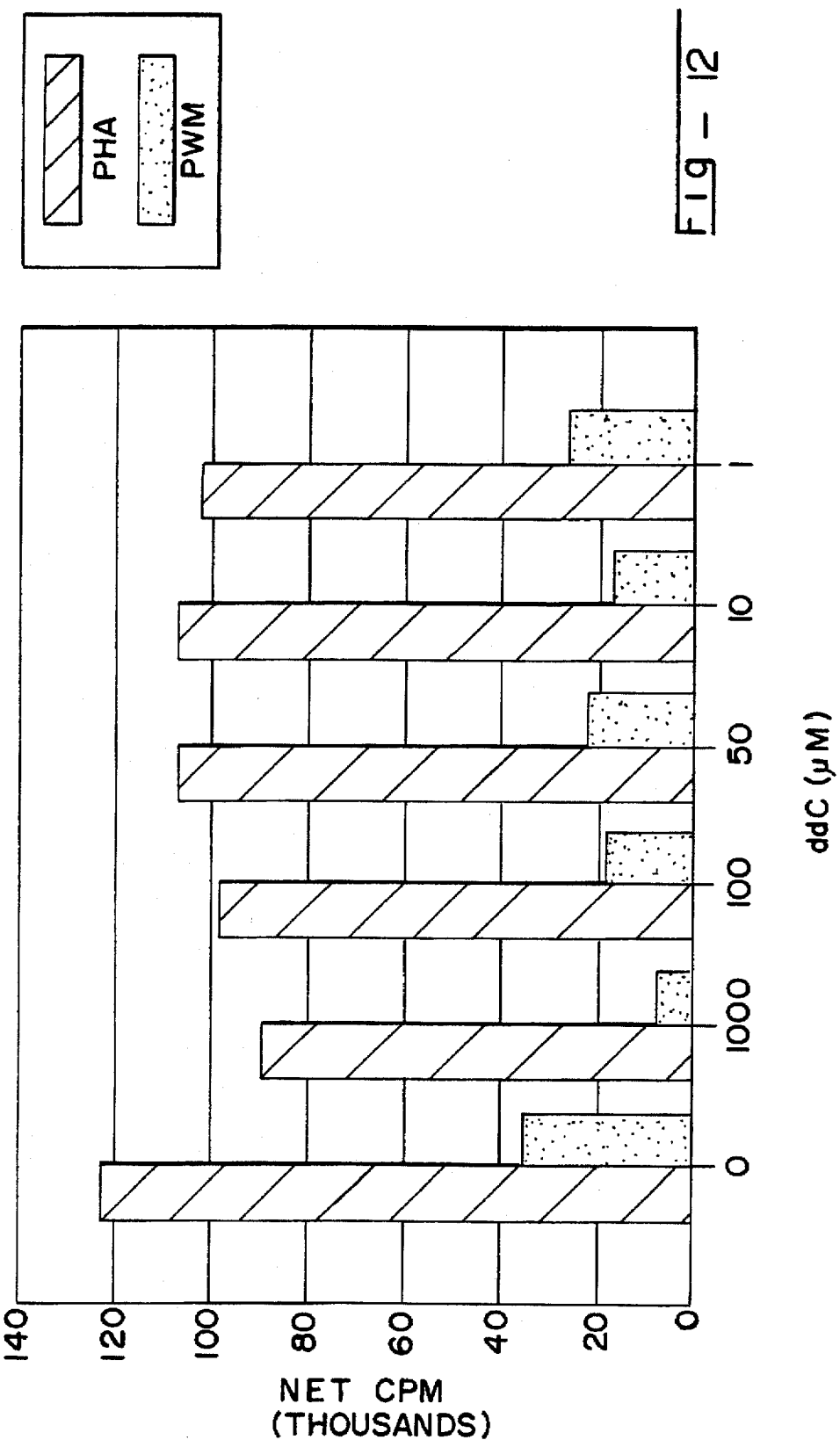

A reduction of 10–25% in T lymphocyte function was seen with a wide range (100–1 µM) of dose levels of ddC. As with AZT, larger reductions in B lymphocyte proliferative responses were observed with ddC. At the 1000 µM concentration an 80 to 85% reduction was seen, and a 20–35% reduction was obtained at the 1 µM dose level of ddC (Charts Ia(e) (xi) and Ia(e) (xii) (FIGS. 11 and 12).

EXPERIMENT Ia(f)

Effects of Drugs on Human Monocyte Function

Monocytes from each human donor were incubated for 30 minutes with three different dose levels of compound Ia in triplicate. These cells were added to agarose and droplets of agarose containing cells were added to small chambers. A chemotaxis agent was added to induce enhanced migration of the mononuclear cells. The detailed assay procedures are described below.

Cell migration patterns of triplicates within 30% of each other were generally accepted. Results are listed in Table Ia(f)(i).

TABLE Ia(f)(i)

| | Spontaneous Migration | Chemotactic Migration (Response to f—met—leu—phe) |
|---|---|---|
| Concentration of IPA (µM) | % Change in Migration Versus Media Control (+ or −) | % Change in Migration Versus Media Control with f—met—leu—phe (+ or −) |
| 1000 | −29% | — |
| 300 | −22% | — |
| 100 | −37% | −71% |
| 30 | −15% | −65% |
| 10 | −2% | −55% |
| 3 | +14% | −45% |
| media | — | — |
| 1 | +73% | −16% |
| 0.3 | +51% | +12% |
| 0.1 | +31% | — |
| media | — | — |

+ = Increased
− = Decreased

There was a 22–37% reduction in the ability of the monocytes to spontaneously migrate using 100–1000 µM concentrations of IPA. There was a smaller 15% reduction in spontaneous migration at the 30 µM concentration of IPA. Enhanced spontaneous migration was observed using 0.1–0.3 µM of IPA The effect of IPA was studied using concentrations of IPA surrounding the initially observed transition level of from 3–30 µM. The results are tabulated in Table Ia(f)(ii).

TABLE Ia(f)(ii)

| Concentration of IPA (µM) | Total Area Migration (mm²) | % Change in Migration with IPA Versus Media Control |
|---|---|---|
| 30 | 5795 | −34% |
| 25 | 6435 | −26% |
| 20 | 6804 | −22% |
| media | 8732 | — |
| 15 | 6300 | −31% |
| 10 | 6846 | −25% |
| 5 | 7952 | −12% |
| media | 9085 | — |

+ = Increased
− = Decreased

As can be seen from Tables Ia(f) (i) and Ia(f) (ii), the degree of decrease in spontaneous migration of cells in the presence of IPA varies somewhat between the two sets of experiments. For example, a 15% decrease was observed in the migration of cells at 30 µM IPA (Table Ia(f) (ii) and a 34% decrease is shown in Table Ia(f) (ii). This size of variation is normal for this type of assay. (Luster, et al, ibid).

The relative effects of AZT and ddC were also studied. The results are tabulated in Table Ia(f) (iii).

TABLE Ia(f)(iii)

COMPARATIVE ABILITIES OF HUMAN MONOCYTES TO FUNCTION (SPONTANEOUSLY MIGRATE) FOLLOWING TREATMENT WITH IPA, AZT, AND ddC

| | % Change in Migration Versus Media Control | | |
|---|---|---|---|
| Concentration | IPA | AZT | ddC |
| 1000 | −52% | −58% | −44% |
| 100 | −36% | −59% | −22% |
| 70 | −41% | — | — |
| 65 | −41% | — | — |
| 60 | −36% | — | — |
| 55 | −41% | — | — |
| 50 | −45% | −57% | −41% |
| 45 | −49% | — | — |
| 40 | −51% | — | — |
| 35 | −52% | — | — |
| 30 | −40% | — | — |
| 10 | +8% | −31% | −45% |
| 1 | +14% | −28% | −36% |

+ = Increased
− = Decreased

DETAILED DESCRIPTION OF HUMAN LYMPHOCYTE BLASTOGENESIS ASSAY

1. Mononuclear cells are separated from whole blood by differential centrifugation using a synthetic separation medium, or are thawed from a cryopreserved preparation. The cells are washed and resuspended in media (RPMI—1640, L-Glutamine 2 mM, Herpes Buffer 25 mM, Gentamicin 50 µg/ml, Human AB Serum-heat inactivated (56°, 300°) 20%).

2. A viable cell count is determined.

3. Cell concentration is adjusted to $2 \times 10^6$ /ml in media.

4. The cell suspension is added to wells of a 96-well flat bottom plate in 0.1 ml aliquots ($2 \times 10^5$ cells).

5. The selected mitogens and/or antigens (in media without serum) are added to the cells in the wells also in 0.1 ml aliquots.

6. The cultures are incubated for 3–7 days (depending upon the mitogen or antigen) at 37° C. in a humidified 5% $CO_2$ atmosphere.

7. Six to eight hours before termination of cultures 0.05 ml (1 µCi) of $^3$HTdR sp. act 6.7 Ci/mM (20 µCi/ml stock) is added to each well.

8. At termination of cultures the cells are harvested onto strips of scintillation-grade fibreglass paper using a multiple sample harvester.

9. Perforated disks from the fibreglass paper of the harvested cultures are placed each into scintillation vials to which is then added 5 ml of toluene based scintillation cocktail.

10. The vials are counted in a liquid scintillation counter for one minute where the amount of incorporated $^3$HTdR is determined.

CALCULATION OF RESULTS $$\% \text{ change} = \frac{\text{net CPM of test individual}}{\text{net CPM of normal individual}} \times 100$$

ISOLATION OF MONOCYTES USING PERCOLL GRADIENT SEPARATION

1. Add 6 ml of Phosphate Buffered Saline (PBS) 2× to 7 ml of Percoll.

2. Add mixture to 15 ml polycarbonate centrifuge tubes (Sorvall *03243, 18×100 mm, pt. *00770 50/box, w/caps).

3. Centrifuge tubes at 21,000× g for 45 minutes (Sorvall, RC2–B centrifuge w/SS-34 rotor, 34 fixed angle, −15,000 rpm w/brake off @4° C.), Percoll gradient is good for two weeks.

4. Mononuclear cells are separated from whole blood by differential centrifugation using a synthetic separation medium.

5. Cells are washed 2× with Basal Salt Solution (BSS).

6. Resuspend cells in BSS+10% BCS, then add mixture to 50 ml centrifuge tubes containing 30–40 ml of Bovine Calf Serum (BCS) and centrifuge at 400× g for 10 minutes.

7. Resuspend cells in BSS without BCS.

8. Determine viable cell number.

9. Adjust concentration of cells to $2.0-2.5 \times 10^4$ ml.

10. Carefully layer 2 ml of cells on top of Percoll gradient. Centrifuge tubes at 100× g for 20 minutes at 4° C. with brake off.

11. Monocyte layer is harvested with a pasteur pipet and aliquoted into a 50 ml centrifuge tube. Dead cells are in the top band. Monocytes are about 5 ml above middle gradient. Lymphocytes are about 5 ml below middle gradient. Do not aliquot more than 6 Percoll gradient tubes of monocytes into one 50 ml centrifuge tube.

12. Wash cells 3× in BSS without BCS.

13. Resuspend cells in desired media.

14. Perform esterase stain on monocyte cell suspension to determine ratio of monocytes. Ratio ranges from 50–80%.

CHEMOTAXIS ASSAY

1. A 0.4% solution of Agarose (Seakem HE) and distilled $H_2O$ is prepared, eliquoted into 1 dram vials, autoclaved and stored at 40° C. until used.

2. A suspension of $3 \times 10^2$ ml cells in Media 199 2× containing glutamine 2 mM, gentamicin 50 g/ml and bovine calf serum-heat inactivated (56° C., 30° C.) 20%, is combined with an equal amount of 0.4% Agarose.

3. A 5 µl droplet of cell/agarose mixture is added to the center of a Sterilin plate (Surrey, England).

4. A 2 µl droplet of agarose/media mixture is added 3–5 mm to one side of the cell/agarose droplet and a 2 µl droplet of agarose/chemo-attractant (N-formyl-L-methionyl-L-Leucyl-L-Phenylalanine $10^{-4}$M(F-Met-Leu-Phe)) is added 3–5mm to the other side of the cell/agarose droplet.

5. The droplets are allowed to solidify, after which 0.5 ml of RPMI-1640 containing glutamine 2 mM, gentamicin 50 µg/ml and bovine calf serum 10% is added to the well. A cover slip is then placed over the well.

6. The plate is incubated at 37° C., 5% $CO_2$/air humified for approximately 18 hours.

7. The plate is removed from the incubator and the distance the cells have moved towards the media control and the chemoattractant droplets is traced and measured.

EXPERIMENT Ia(g)

M413 Cells, CMV, Visual Method

Confluent monolayers of M413 cells (a type of dipliod human fibroblast cells) in 48 well microtiter plates were used. They were grown in Dulbecco's MEM (minimum essential medium) supplemented with 10% fetal bovine serum and 50 µg/ml gentamicin.

Stock cytomegalovirus (CMV) was diluted in a series of 10-fold dilutions in the above medium, and 0.1 millimolar amounts were added to the wells of the microtiter plates and allowed to absorb virus for 90 minutes at 37° C.

Unabsorbed virus was removed by aspiration and 0.5 ml of medium containing dilutions of drug was added to duplicate wells at each concentration of virus.

After incubating for 5 days, fresh medium was added to each well, no additional drug being included, and the plates were scored for cytopathic effects the next day. The viruses produce characteristic enlarged rounded cells in a cellular background that is completely devoid of such cells.

The data were expressed as the reciprocal of the greatest dilution producing any of the characteristic rounded cells (the "titer"), and the percent inhibition was calculated by comparing the experimental titer with the control titer, with intermediate results interpreted as those of Experiment Ia(a). The results are summarised it, Table Ia(g).

Experiments were carried out to determine the viability of uninfected cells under the conditions of these experiments.

Uninfected cells were exposed to different concentrations of IPA and their viability was determined 24 hours later, relative to control cells, by trypan blue exclusion TABLE Ia(g)

| Concentration of IPA | Titer | Percent Inhibition | Percent Viable Cells |
| --- | --- | --- | --- |
| 0 | $3 \times 10^3$ | | 94 |
| 1000 µM | <10 | >99.7 | 23 |
| 300 µM | $3 \times 10$ | 99 | 50 |
| 100 µM | $3 \times 10^2$ | 90 | 75 |
| 30 µM | $3 \times 10^3$ | 0 | 90 |
| 10 µM | $3 \times 10^3$ | 0 | 95 |

EXPERIMENT Ia(h)

M413 Cells, HSV-I, Visual Method

A procedure similar to that described for Experiment Ia(g) was followed except herpes simplex virus-type I (HSV-I) was used. The results are given in Table Ia(h).

Experiments to determine the viability of uninfected cells under these conditions were carried out and are listed in Table Ia(g).

TABLE Ia(h)

| Concentration of IPA | Titer | Percent Inhibition (HERPES SIMPLEX TYPE-1) |
| --- | --- | --- |
| 0 | $3 \times 10^4$ | |
| 1000 µM | <10 | >99.97 |
| 300 µM | <10 | >99.97 |
| 100 µM | $3 \times 10$ | 99.9 |
| 30 µM | $3 \times 10^4$ | 0 |
| 10 µM | $3 \times 10^4$ | 0 |

EXPERIMENT Ia(i)

P$_3$HR1 Cells acutely infected with EBV, Immunofluorescence

Experiments were carried out using concentrated P$_3$HR1 cells. The virus was titered by superinfection of the Raji cell line which contains EBV genomes but which does not express any EBV proteins except the nuclear antigen (EBNA). Infection of Raji cells by infectious EBV induces early antigens (EA) in the cells in proportion to the titer of infectious virus. EA was detected using a monoclonal antibody.

The assay was set up with Raji cells exposed for 2 hours to serial 10 fold dilutions of the P$_3$HR1 virus. Excess virus was separated by centrifugation and removed. Aliquots of cells infected at each dilution were distributed into 12 well trays (0.5 ml/well), and 0.5 ml of medium containing twice the desired final medium concentration was added to each well.

At 24 and 72 hours, aliquots of each well were washed, added to Teflon® outlined wells on a glass slide, air dried to attach them to the glass, and then fixed with acetone-methanol (50:50). Standard immunofluorescence procedures were followed to quantify the percent of cells containing virus at each time, virus dilution and drug concentration. The results are presented in Table Ia(i).

TABLE Ia(i)

| Concentration of IPA | Virus Dilution | Percent Positive 24 Hours | Cells 72 Hours | Titer at 72 Hours |
| --- | --- | --- | --- | --- |
| 0 | $10^{-1}$ | 50* | 65 | $10^6$ |
| | $10^{-2}$ | 13 | 25 | |
| | $10^{-3}$ | 3 | 10 | |
| | $10^{-4}$ | 1 | 5 | |
| | $10^{-5}$ | 0 | 1 | |
| | $10^{-6}$ | 0 | <1 | |
| 1000 µM | $10^{-1}$ | 0 | <1 | $10^4$ |
| | $10^{-2}$ | 0 | <1 | |
| | $10^{-3}$ | 0 | <1 | |
| | $10^{-4}$ | 0 | <1 | |
| | $10^{-5}$ | 0 | 0 | |
| | $10^{-6}$ | 0 | 0 | |
| 300 µM | $10^{-1}$ | 2 | 7 | $10^5$ |
| | $10^{-2}$ | 1 | 7 | |
| | $10^{-3}$ | <1 | 3 | |
| | $10^{-4}$ | 0 | <1 | |
| | $10^{-5}$ | 0 | <<1 | |
| | $10^{-6}$ | 0 | 0 | |
| 100 µM | $10^{-1}$ | 6 | 15 | $10^6$ |
| | $10^{-2}$ | 3 | 10 | |
| | $10^{-3}$ | <1 | 2 | |
| | $10^{-4}$ | 0 | 1 | |
| | $10^{-5}$ | 0 | <1 | |
| | $10^{-6}$ | 0 | <1 | |
| 30 µM | $10^{-1}$ | 10 | 20 | $10^6$ |
| | $10^{-2}$ | 3 | 10 | |
| | $10^{-3}$ | 1 | 7 | |
| | $10^{-4}$ | <1 | 4 | |
| | $10^{-5}$ | 0 | <1 | |
| | $10^{-6}$ | 0 | <1 | |
| 10 µM | $10^{-1}$ | 17 | 28 | $10^6$ |
| | $10^{-2}$ | 8 | 15 | |
| | $10^{-3}$ | 2 | 8 | |
| | $10^{-4}$ | <1 | 5 | |
| | $10^{-5}$ | 0 | <1 | |
| | $10^{-6}$ | 0 | <1 | |

These percentage values were obtained by counting about 200 cells at each point and calculating the percentage of cells that are antigen positive.

EXPERIMENT Ia(i)

M413 Cells, HSV-1, Immunofluorescence Assay

The experiments were performed in duplicate M413 cells which were set up in Titer-Tek slides (4 well, glass) and those that were confluent within one day were used in experiments. Within 24–48 hours, cell densities were checked to ensure sufficiency to proceed with infection. Stock HSV-1 was serially diluted in 10-fold steps (1, $10^{-1}$, $10^{-2}$, $10^{-3}$, $10^4$) to provide 2 ml of each dilution: 0.2/1.8 ml diluent to finally yield overall dilutions of approximately $10^{-1}$, $10^{-2}$, $10^{-3}$, $10^{-4}$, $10^{-5}$. Virus absorption was allowed for 90 minutes at 37° C., after which time, the inoculum was removed and replaced with solutions containing IPA at the concentrations as indicated in Table Ia(j). The slide was incubated for 3 days and stained with the following antisera: monoclonal antibody (MAB) to HSV-1 virus capsid antigen (VCA) at 1:20; control mores IgG at 1:20. The results are reported in Table Ia(j).

TABLE Ia(j)

| | Log Virus Dilution | | | | |
|---|---|---|---|---|---|
| Concentration | −1 | −2 | −3 | −4 | −5 |
| Controls (no IPA): | | | | | |
| MAB-VCA | 2.5 | 2 | 2 | 2 | 0.5 |
| Normal Mouse IgG | 0 | 0 | 0 | 0 | 0 |
| Uninfected MAB-VCA | 0 | | | | |
| 1000 μM | 0 | 0 | 0 | 0 | 0 |
| 300 μM | 0 | 0 | 0 | 0 | 0 |
| 100 μM | 0 | 0 | 0 | 0 | 0 |
| 30 μM | 0 | 0 | 0 | 0 | 0 |
| 10 μM | 0 | 0 | 0 | 0 | 0 |
| 3 μM | 0 | 0 | 0 | 0 | 0 |
| 1 μM | 0.25 | 0.25 | 0.25 | 0.25 | 0.25 |

A similar series of tests were performed using acycloguanosine (Acyclovir) for comparison purposes. These results are shown in Table Ia(jb).

TABLE Ia(jb)

Immunofluorescence measurement of HSV-1 grown on human fibroblasts and exposed to Acyclovir.

| | IMMUNOFLUORESCENCE AT A VIRUS DILUTION OF: | | | | | |
|---|---|---|---|---|---|---|
| CONC. | −3 | −4 | −5 | −6 | −7 | TITER |
| NONE | 4+/4+ | 4+/4+ | 4+/4+ | 4+/4+ | 4/4 | >$10^8$ |
| 1000 | 0/0 | 0/0 | 0/0 | 0/0 | 0/0 | <$10^3$ |
| 300 | 0/0 | 0/0 | 0/0 | 0/0 | 0/0 | <$10^3$ |
| 100 | 0/0 | 0/± | 0/0 | 0/0 | 0/0 | <$10^3$ |
| 30 | 0/± | 0/0 | 0/0 | 0/0 | 0/0 | <$10^3$ |
| 10 | 1/1 | 0/1 | 0/1 | 0/3 | 0/1 | $10^7$ |
| 3 | 2/2 | 2/3 | 2/2 | 3/3 | 1/3 | >$10^7$ |
| 1 | 3/3 | 3/3 | 2/3 | 2/2 | 2/2 | >$10^7$ |

LEGEND:
1 = LESS THAN 10 POSITIVE CELLS PER SLIDE
2 = GREATER THAN 10 CELLS, OR SMALL CLUSTERS OF + CELLS.
3 = LARGE FOCI OF FLUORESCENT CELLS, EVIDENT CPE.
4 = WIDESPREAD FLUORESCENCE, MANY FOCI.

EXPERIMENT Ia(k)

M413 Cells, CMV, Immunofluorescence Assay

The procedure described for Experiment Ia(j) was followed with cytomegatovirus (CMV) substituted for MAB to HSV-1.

TABLE Ia(k)

| | Log Virus Dilution | | | | |
|---|---|---|---|---|---|
| Concentration | −1 | −2 | −3 | −4 | −5 |
| Controls (no IPA): | | | | | |
| MAB-VCA | 4 | 3.5 | 3 | 2.5 | 2 |
| Normal Mouse IgG | 0 | 0 | 0 | 0 | 0 |
| Uninfected MAB-VCA | 0 | | | | |
| 1000 μM | 0.5 | 0.5 | 0.25 | 0 | 0 |
| 300 μM | 2 | 1.5 | 1 | 0.5 | 0.25 |
| 100 μM | 2 | 1.5 | 1 | 0.5 | 0.5 |
| 30 μM | 2 | 2 | 1.5 | 1 | 1 |
| 10 μM | 3 | 3 | 3 | 2 | 2 |

TABLE Ia(k)-continued

| | Log Virus Dilution | | | | |
|---|---|---|---|---|---|
| Concentration | −1 | −2 | −3 | −4 | −5 |
| 3 μM | 3.5 | 3 | 3 | 2 | 2 |
| 1 μM | 4 | 3.5 | 3 | 2.5 | 2 |

EXPERIMENT Ia (1)

Test of IPA on HIV-1 infected 81-66-45 cells.

The 81-66-45 cell line is an HTLV-1 transformed non-producer. The procedure of Experiment 1a(a) was followed. The results are summarised in Table Ia(1).

TABLE Ia(1)

| Drug | | | Percent Inhibition |
|---|---|---|---|
| None | | | |
| AZT | 100 μM | <10 | >99.9 |
| AZT | 30 μM | <01 | >99.9 |
| ddC | 100 μM | <10 | >99.9 |
| ddC | 30 μM | <10 | >99.9 |
| IPA | 1000 μM | <10 | >99.9 |
| IPA | 300 μM | <10 | >99.9 |
| IPA | 100 μM | <10 | >99.9 |
| IPA | 30 μM | <10 | >99.9 |
| IPA | 10 μM | 1 × 10 | 90 |
| IPA | 3 μM | 1 × 10 | 0 |
| IPA | 1 μM | 1 × 10 | 0 |

EXPERIMENT Ia(m)

Stability Tests of IPA

Infrared spectra of IPA, taken from time to time, as described below, were used to monitor changes which may have occurred in the IPA over time. The compound was generally stored at −10° C. FT-IR data of fresh IPA are listed in the first column of Table Ia(m). A second FT-IR spectrum of the same compound, after storage at −10° C. for 110 days, was taken and the data are listed in the second column of Table Ia(m). The melting point of the compound was taken at the same time. The original melting point was 128°–130° C., and the second melting point, 110 days later, was 129°–132° C.

As can be seen from Table Ia(m), there was little change in the FT-IR spectrum of the compound and no significant change in the melting point of the compound. The observed melting points compare favourably with literature melting points ranging from 126° C. to 138° C.

TABLE Ia(m)

| FT-IR Peak Wavelengths in μM for Samples of IPA | |
|---|---|
| Fresh IPA | After Storage for 110 days at −10 C. |
| 1626 | 1626 |
| 1537 | 1537 |
| 1475 | 1475 |
| 1420 | 1419 |
| 1381 | 1381 |
| 1337 | 1338 |
| 1295 | 1294 |
| 1270 | 1270 |
| 1221 | 1221 |
| 1184 | 1184 |

TABLE Ia(m)-continued

FT-IR Peak Wavelengths in μM for Samples of IPA

| Fresh IPA | After Storage for 110 days at −10 C. |
|---|---|
| 1098 | 1099 |
| 1079 | 1079 |
| 1057 | 1057 |
| 1031 | 1032 |
| 986 | 986 |
| 961 | 961 |
| 865 | 866 |
| 823 | 824 |
| 794 | 793 |
| 763 | 763 |
| 713 | 714 |
| 668 | 668 |
| 641 | 639 |
| 555 | 555 |
| 434 | 434 |

ADDITIONAL IN-VITRO TESTS ON IPA

The effect of the drug IPA on HIV-1 replication was examined in vitro in acutely and persistently infected cells. Production of HIV-1 in culture supernatant was determined by the presence of HIV P24.

Methods

In vitro infection of H9 cells was carried out as described previously. Briefly, $5\times10^6$ H9 cells were treated with DEAE-dextran (25 μg/ml) for 20 min. Cells were then infected with 1 ml of cell free HIV-1 ($1\times10^5$ RT unit) for 1 hr at 37° C. Cells were then washed and incubated for 12 days in the absence or presence of various concentrations of IPA. Every 3–4 days medium was replaced with fresh medium containing appropriate concentrations of drug. At various days following infection, the presence of HIV-1 in the supernatant was monitored by measuring HIV-1 P24 using the antigen capture test (DuPont®, Wilmington, Del.).

HIV-1 production from an AIDS patients' lymphocytes was carried out as described previously. Briefly, $10\times10^6$ patients' lymphocytes were cocultured with $5\times10^6$ PHA-stimulated normal PBL in RPMI 1640 medium containing 20% FBS, 5% interleukin 2 (Cellular Products, Buffalo, N.Y.) and various concentrations of IPA. The culture was continued for 4 weeks. The culture was fed twice a week with $2-3\times10^6$ PHA-stimulated normal PBL. Culture medium was withdrawn twice a week and tested for the presence of HIV by the antigen capture test. Culture medium was replaced with new medium with or without drug at 3–4 days intervals.

To examine the effect of IPA on the production of HIV-1 in H9 cells persistently infected with HIV-1, $5\times10^6$ HIV-1-infected H9 cells were incubated in the absence or presence of IPA. Every 4–5 days, two thirds of the total cells were removed and medium was changed. New medium with or without drug was added to bring up to the original volume. At days indicated, culture supernatant was withdrawn and tested for the production of HIV-1 by the RT activity. A 20,000 cpm or more TCA insoluble radioactivity per milliliter of supernatant was considered positive in the RT assay.

Results

Figure 13:
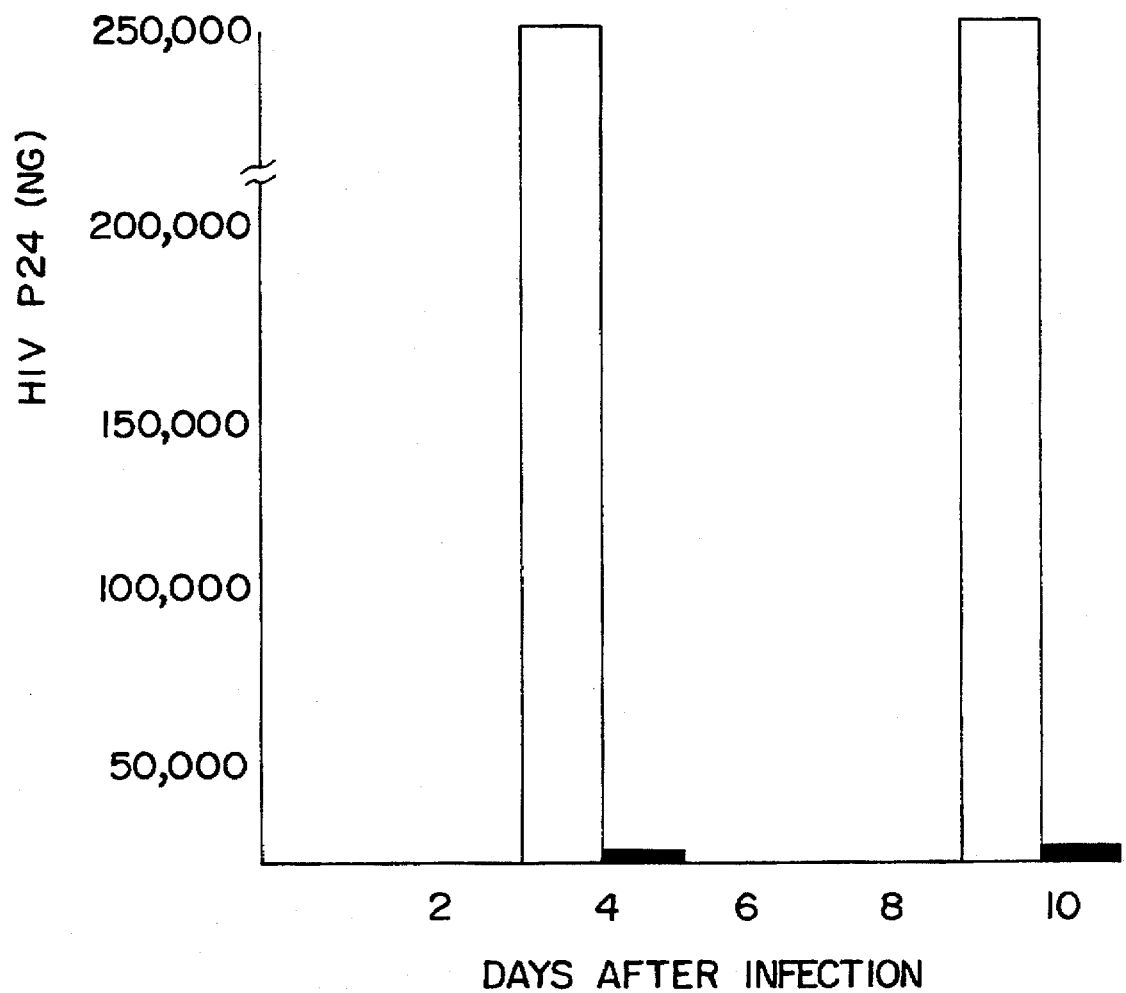
FIG. 13 is a graph of effects of IPA on in-vitro HIV infection of H9 cells.

An investigation of the effect of IPA on in-vitro HIV-1 infection of H9 cells, a T cell line, was performed. The drug was added following 1 hr adsorption of the virus, and was maintained in the culture medium throughout the incubation period. As shown in FIG. 13, IPA inhibited in vitro HIV-1 infection in a dose dependent manner. A more than five log inhibition of HIV-1 production was obtained at doses of 3.75 μM or higher.

IPA at concentrations of 30 μM or lower did not have any significant cytotoxic effect on the growth of viable PHA stimulated PBL up to 10 days in culture (Table G1).

Figure 14:
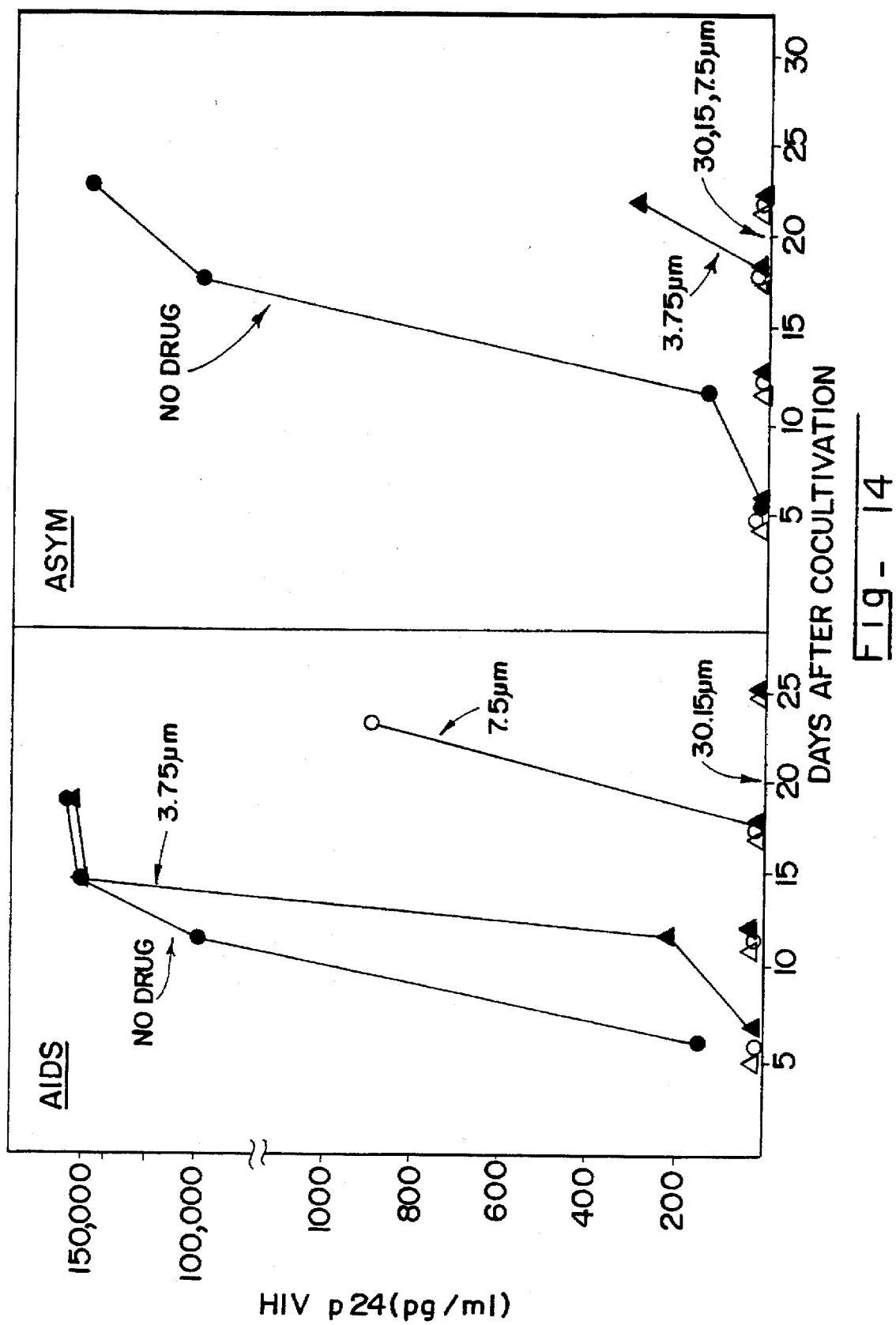
FIG. 14 is a graph of effects of IPA on HIV production.

A study of IPA inhibition of HIV-1 production from lymphocytes of a HIV-1 seropositive patient was carried out. For this purpose, lymphocytes from an AIDS patient and an asymtomatic patient were cocultured with PHA stimulated PBL in the presence or absence of IPA. Results shown in FIG. 14 indicate that IPA inhibited HIV-1 production in a dose dependent manner. Virus production, as determined by the HIV-1 P24 antigen capture assay, was completely blooked by IPA at concentrations of 3.75 μM or higher. In contrast, HIV-1 was detected in untreated cultures as early as 7 days following cocultivation.

The effect of IPA on replication of HIV-1 was also examined in H9 cells that were persistently infected with HIV-1 (H9-HIV-1). No cytotoxicity was observed up to 30 days in H9-HIV-1 cells incubated with IPA at concentrations of 30 μM and lower, as judged by the measurement of viable cell number.

These results demonstrate IPA to be an active anti HIV-1 agent, capable of suppressing in vitro infection by extracellular virus as well as HIV-1 production from lymphocytes of seropositive men. It has recently been shown that during cocultivation of lymphocytes from HIV-1-infected patients with normal mitogen stimulated PBL, spread of HIV-1 from infected cells to uninfected cells occurs by cell-to-cell transmission, as well as by infection through extracellular virus. AZT inhibits HIV-1 infection by extracellular virus, but has no effect on virus growth following cell-to-cell transmission of HIV-1. The fact that IPA inhibits HIV-1 production from infected patients' lymphocytes indicates that the drug not only inhibits infection by extracellular virus but also blocks virus production resulting from cell-to-cell transmission of HIV-1.

TABLE G1

Effect of IPA on the growth of PBL and H9 cells

| IPA Conc. (μM) | Following in-vitro* infection of H9 | Following cocultivation of** patients PBL with PHA-PBL |
|---|---|---|
| 0 | $3.4 \times 10^6$ | $2.9 \times 10^6$ |
| 3.75 | $3.4 \times 10^6$ | $2.9 \times 10^6$ |
| 7.5 | $3.5 \times 10^6$ | $2.8 \times 10^6$ |
| 15 | $3.3 \times 10^6$ | $2.8 \times 10^6$ |
| 30 | $2.7 \times 10^6$ | $2.7 \times 10^6$ |

*Number of viable cells were measured by trypan blue exclusion method, following in-vitro infection of H9 cells from FIG. 13. Number of cells recovered after 10 days.
**Number of cells recovered at 10 days following co-cultivation of lymphocytes of an AIDS patient with PHA-stimulated normal PBL from FIG. 14.

TABLE G2

EFFECT OF IPA ON HIV PRODUCTION FROM H9 CELLS PERSISENTLY INFECTED WITH HIV

| DRUG CONCENTRATION | HIV PRODUCTION RT ACTIVITY cpm/ml | |
|---|---|---|
| | 15 DAYS p.d. | 25 DAYS p.d. |
| 0 | $3 \times 10^5$ | $1.1 \times 10^6$ |
| 3.75 | $2.3 \times 10^5$ | $1.2 \times 10^5$ |
| 7.5 | $2.9 \times 10^5$ | $3.2 \times 10^5$ |
| 15 | $2.3 \times 10^5$ | $3.6 \times 10^5$ |
| 30 | $2.9 \times 10^5$ | $2.5 \times 10^5$ | p.d. = POST DRUG TREATMENT

Summary of Results and Data Manipulation

Figure 15:
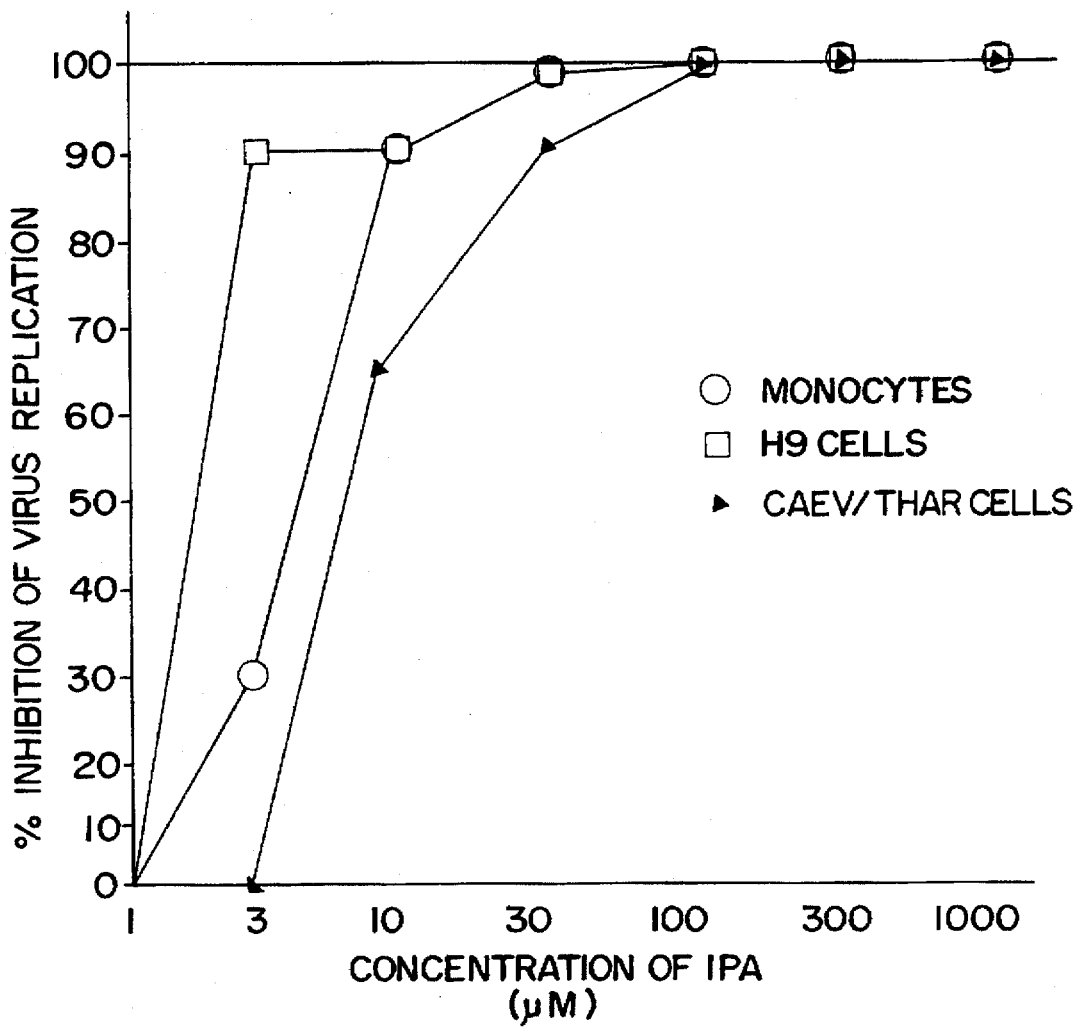
FIG. 15 is a graph of inhibition of virus replication versus concentration of IPA in an assay.

Selected results presented in Tables Ia(a), Ia(b) and Ia(c) are plotted in FIG. 15. These results do not take into account any possible toxic effects of IPA. Reading from FIG. 1, $IC_{50}$ and $IC_{90}$ values can be determined and are listed in Table A.

TABLE A $IC_{50}$ and $IC_{90}$ Values for IPA as read from FIG. 15

| Cell Line | Virus | $IC_{50}$ | $IC_{90}$ |
|---|---|---|---|
| Monocytes | HIV-1 | 6 μM | 10 μM |
| H9 | HIV-1 | 2 μM | 3 μM |
| Himalayan Tahr Ovary | CAEV | 8 μM | 30 μM |

It is apparent from FIG. 15 that IPA appears to inhibit the replication of HIV-1 and CAEV at concentrations ranging from 3 to 30 μM and above. Without appropriate toxicity data it is not possible to calculate the therapeutic index at the various drug concentrations. Nevertheless, the $IC_{50}$ can be seen to vary between approximately 2–6 μM, depending upon the virus and cell line, and the $IC_{90}$ varies between 3–30 μM in these experiments.

Results from Experiment Ia(b) (Table Ia(b) (ii)) and Experiment Ia(I) (Table Ia(i)) are summarised in Summary Table 1.

The "Percent Dead Cells" are taken from Tables Ia(d) (iii) and Ia(d) (v) using the 10-day value, and the therapeutic index have been calculated for each drug concentration. The results of IPA are also graphed in FIGS. 16 and 17. Cytotoxicity (the dashed line) is calculated as the percent live cells.

Figure 16:
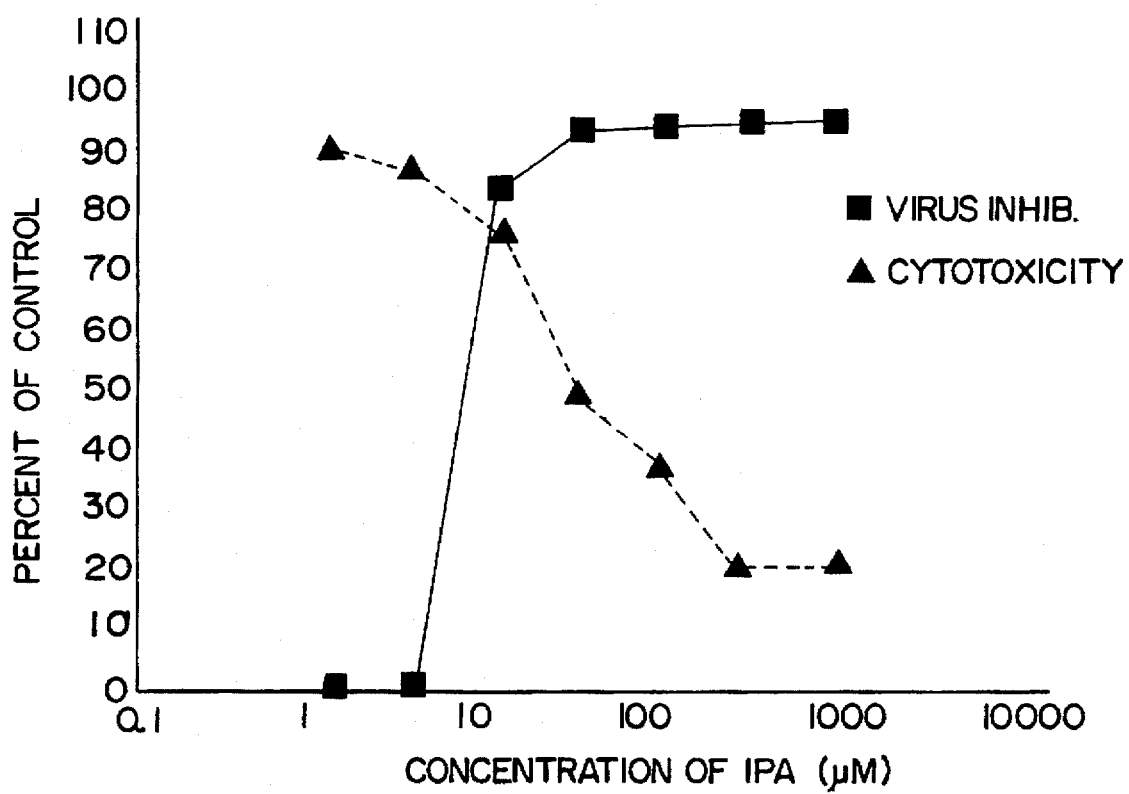
FIG. 16 and 17 are graphs of cytotoxicity and virus inhibition versus concentration of IPA in an assay.
Figure 17:
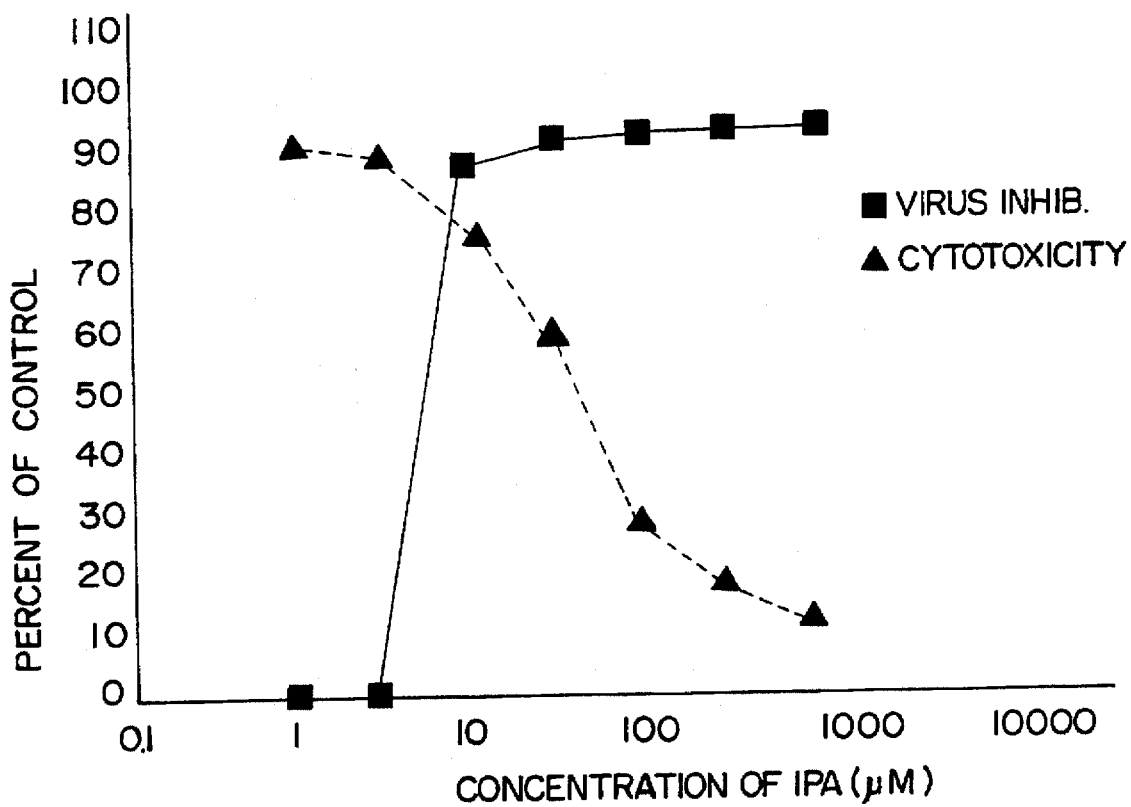
Figure 18:
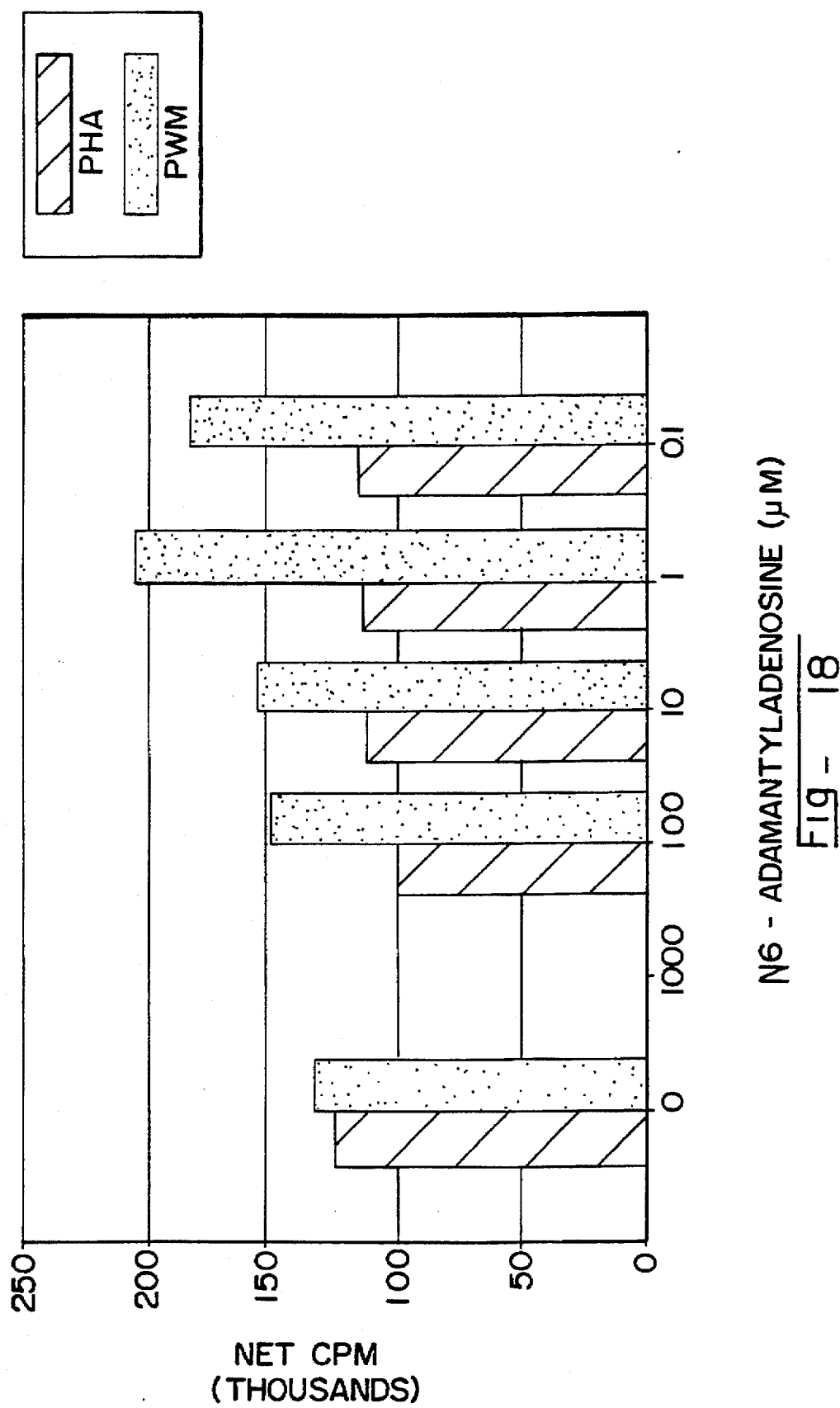
FIG. 18 is a graph of human T and B lymphocyte function versus concentration of $N^6$-adamantyladenosine in an assay.
Figure 19:
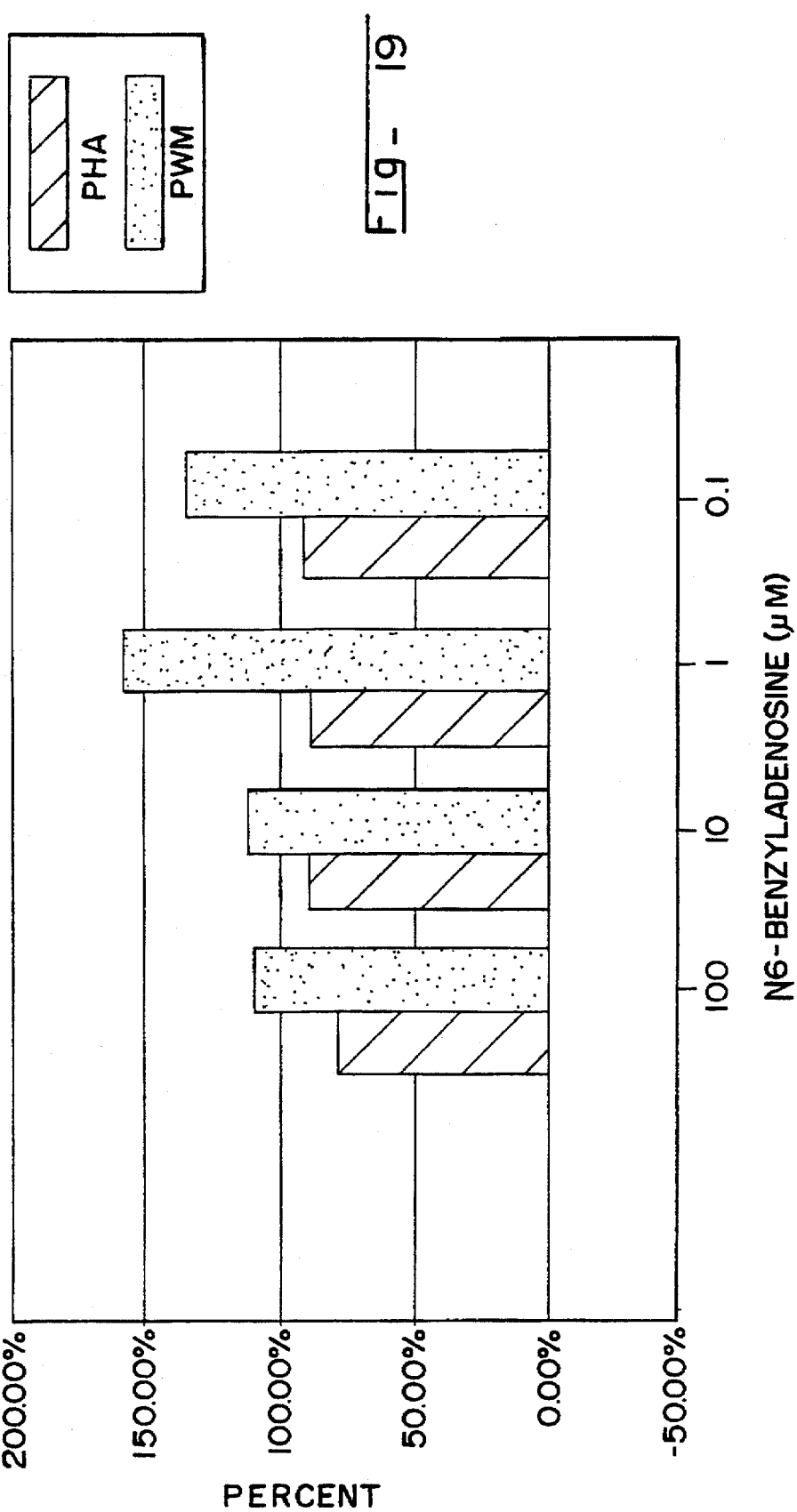
FIG. 19 is a graph of human T and B lymphocyte function versus concentration of $N^6$-benzyladenosine in an assay.
Figure 20:
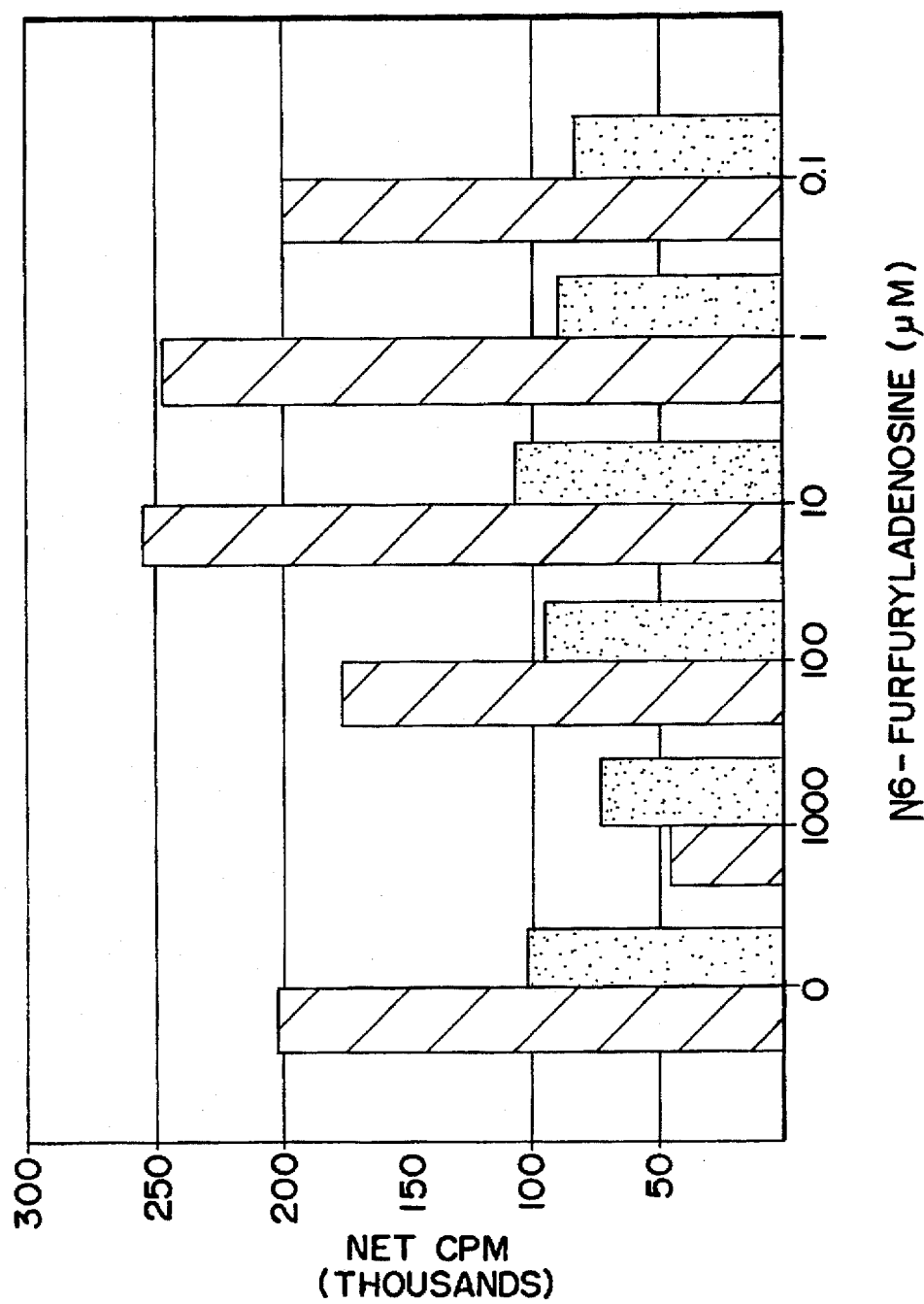
FIG. 20 is a graph of human T and B lymphocyte function versus concentration of $N^6$-furfuryladenosine in an assay.
Figure 21:
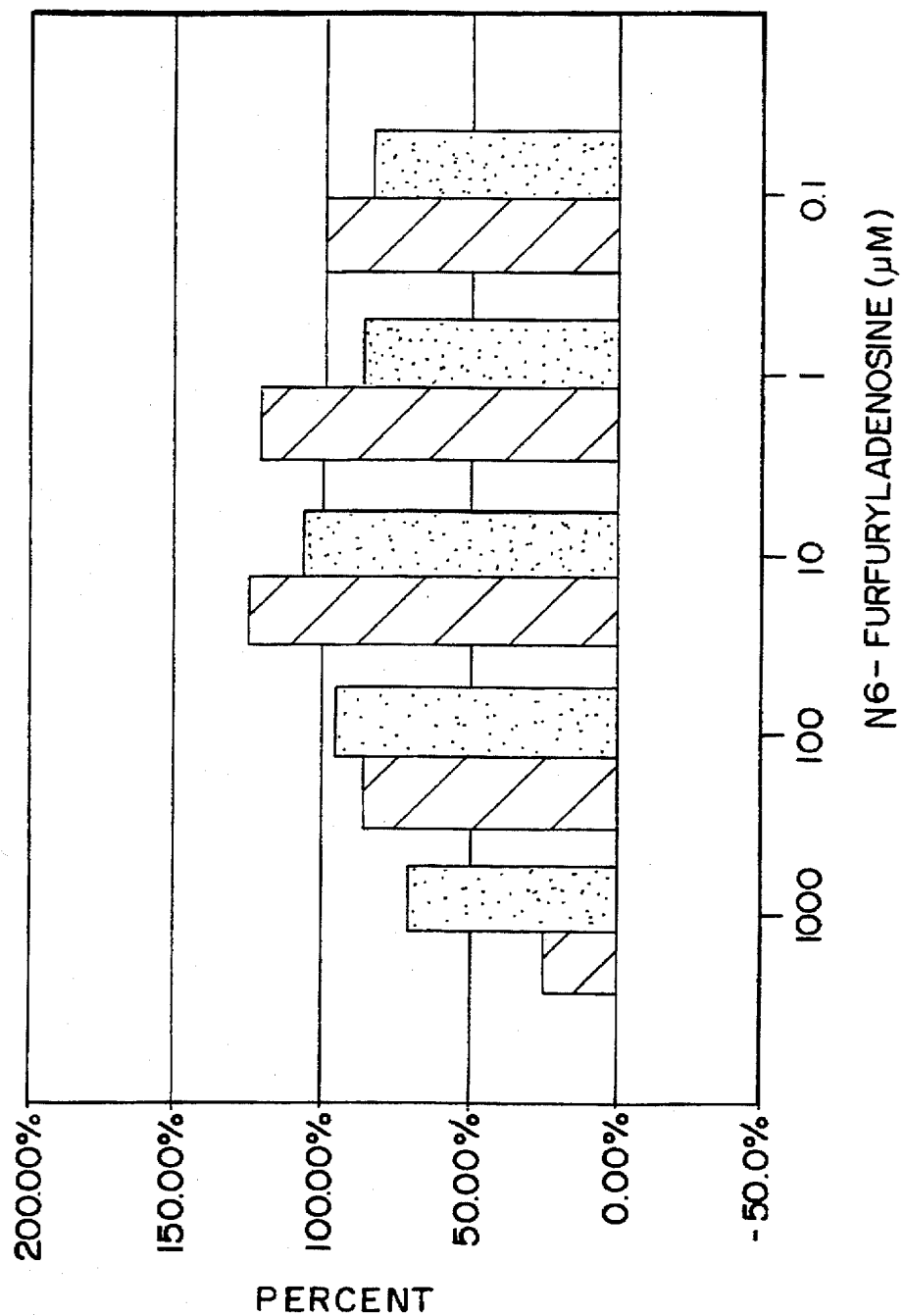
FIG. 21 is a graph of human T and B lymphocyte function versus concentration of $N^6$-furfuryladenosine in an assay.
Figure 22:
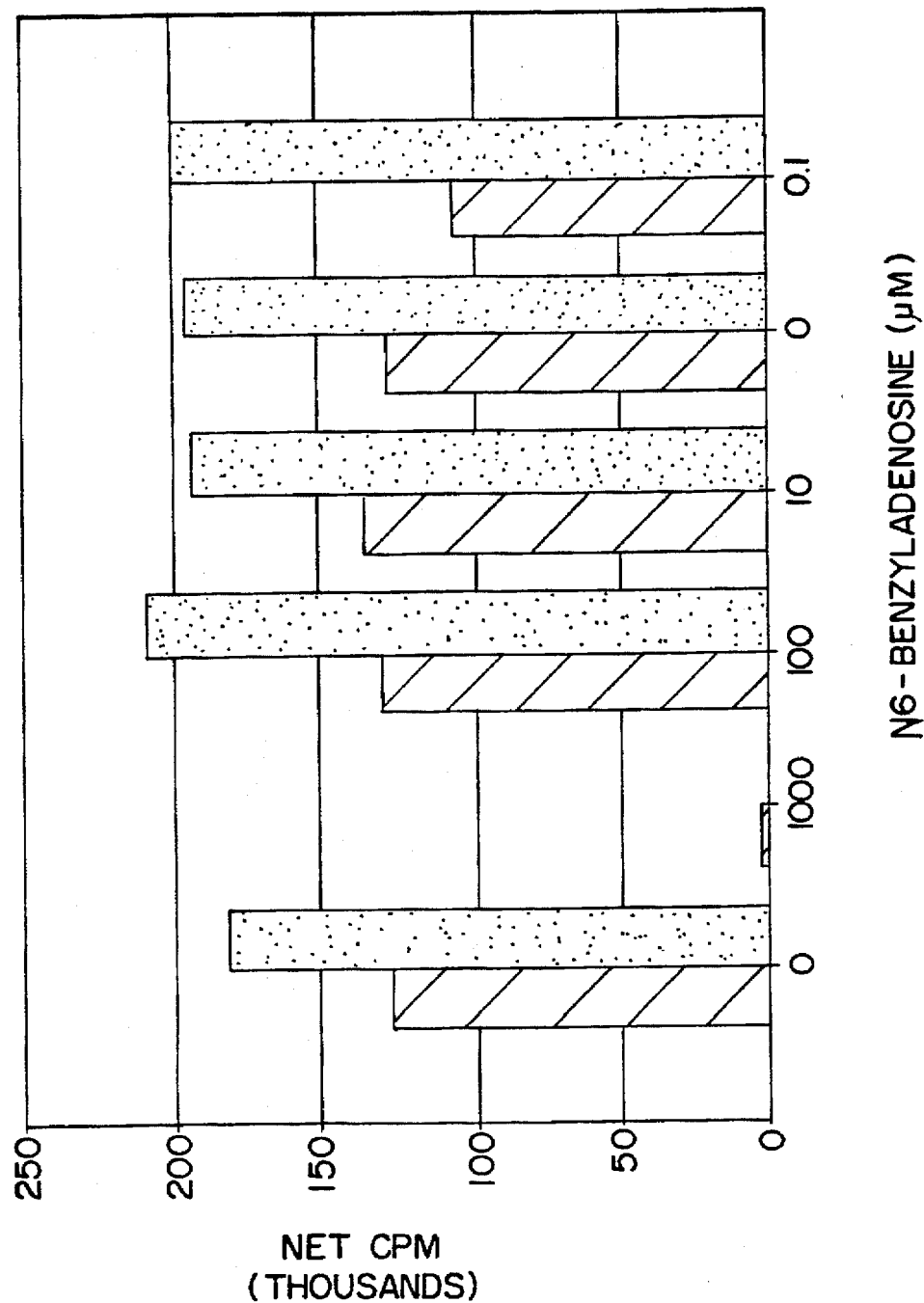
FIG. 22 is a graph of human T and B lymphocyte function versus concentration of $N^6$-benzyladenosine in an assay.
Figure 23:
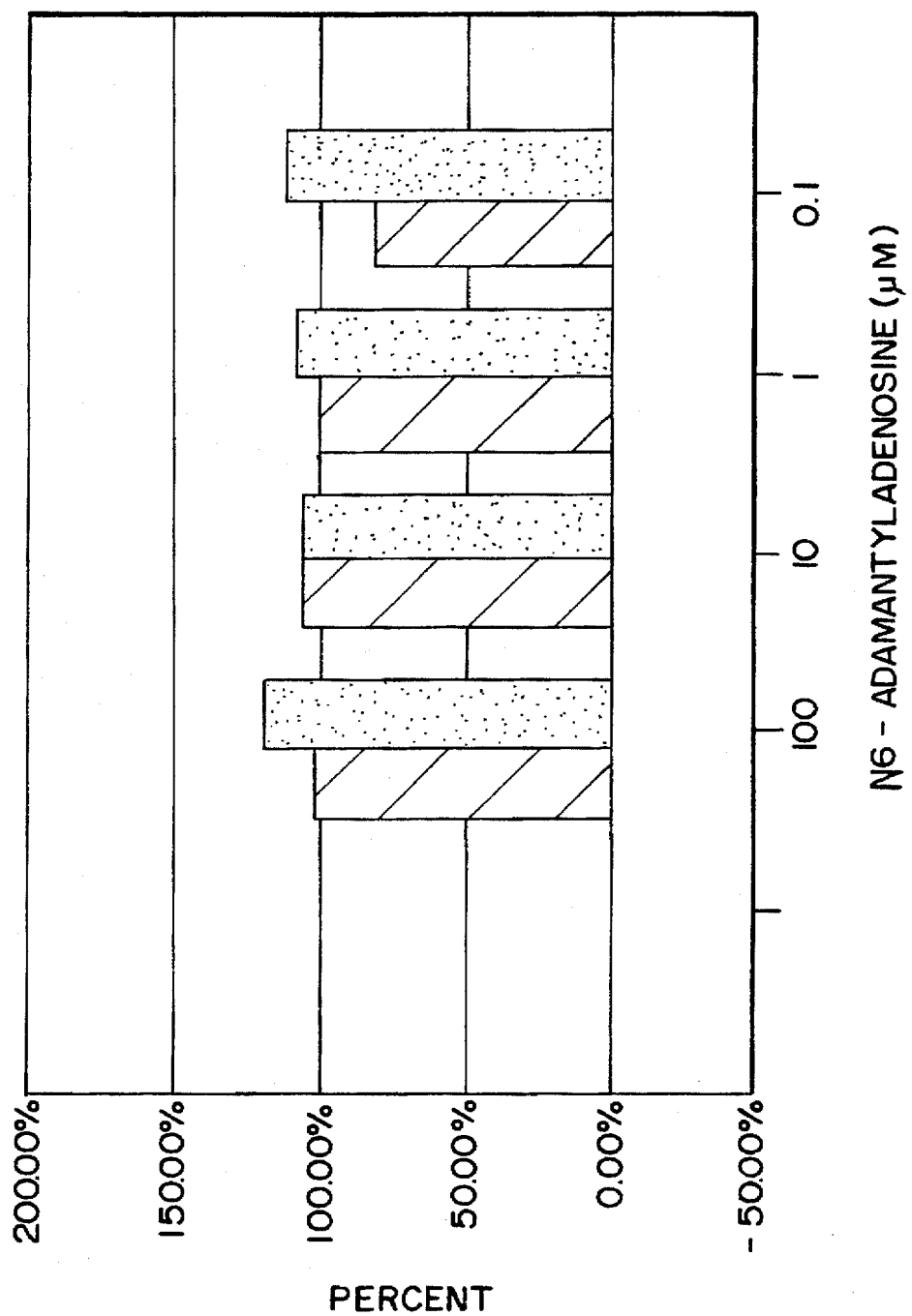
FIG. 23 is a graph of human T and B lymphocyte function versus concentration of $N^6$-adamantyladenosine in an assay.

The availability of toxicity data collected in the same time frame as required for determination of antiviral effectiveness allowed determination of values for two different cell lines. FIGS. 16 and 17 illustrate the curves obtained by plotting the cytotoxicity of IPA (as a percent of the control cell viability) versus the percent of inhibition of HIV-1 replication (as a percent of the control titer) when H9 and 81-66-45 cells were tested. The cytotoxicity data obtained with 10 days continuous exposure, using uninfected cells, were used since 10 days was the length of time required to carry out the infectivity test. As is apparent from Tables Ia(d) (ii)–Ia(d) (v), toxicity is much lower when the drug is added to cells for one day and then removed, or when cells are exposed for only 1 or 4 days. It is difficult to mimic in-vivo exposure times, particularly if metabolites are more toxic that the parent compound and are readily cleared in-vivo but not in-vitro.

Analysis of FIGS. 16 and 17 permit a list of the inhibition values for the two cell lines to be calculated as follows:

| | H9 Cells | 81-66-45 Cells |
|---|---|---|
| $IC_{50}$* | 6 μM | 6 μM |
| $IC_{90}$** | 10 μM | 10 μM |
| $ID_{50}$*** | 50 μM | 40 μM |
| $IC_{50}/ID_{50}$ | 0.12 | 0.20 |

*$IC_{50}$ - The concentration of IPA which inhibits the replication of HIV-1 by 50%.
**$IC_{90}$ - The concentration of IPA which inhibits the replication of HIV-1 by 90%.
***$ID_{50}$ - The concentration of IPA which kills 50% of the cells.

EXPERIMENTS INVOLVING COMPOUNDS Id, Ig, Ih AND II

About 100 ml of solution containing about $5 \times 10^7$ 81-66-45 cells were pelleted by centrifugation, resuspended in 35 ml and divided into 5 ml aliquots. Six of the seven 5 ml aliquots were centrifuged again and the pellets which formed were each suspended in 5 ml of HIV-1, serially diluted in 10 fold steps starting with undiluted virus. Serial dilutions of the virus were made using complete medium containing 10 g/ml of polybrene. The cells were then incubated at 37° C. for 1.5 hour, with occasional shaking. The aliquots were centrifuged again and the pellets which formed were each suspended in 35 ml of fresh medium, RPMI 1640 and 10% FBS. These stock dilutions were then used with each of the compounds being tested, being distributed onto a 24 well tray with 0.25 ml per well.

To each well was added 0.25 ml of drug solution prepared as described below at concentration. In the preparation of stock drug solutions, water soluble compounds were dissolved to make solutions of 10 μM. If necessary, ethanol dimethyl sulfoxide (DMSO) were used to dissolve a compound. Stock drug solutions were serially diluted in 10 fold concentration steps as indicated in the Tables below. A two fold dilution of the drug takes place on addition of 0.25 ml of each solution to each well, which already contains 0.25 ml of virus solution.

The seventh aliquot of cell suspension, uninfected by virus was used to determine drug effects on uninfected cells. To each well in a row of wells, each well containing 0.25 ml of cell suspension, was added 0.25 ml of drug solution, serially diluted.

The titer of HIV-1 at each level was determined using radio immunofluorescence (RIA) after 10 days and the viability of uninfected cells in the presence of each drug was determined.

Results of the above experiments are tabulated in Tables Id(i), Ig(i), Ih(i) and II(i) below.

TABLE Id(i)

Benzyladenosine

| CONCENTRATION μM | TITER | PERCENT INHIBITION | Viability |
|---|---|---|---|
| 1000 | $10^3$ | 90–99 | 80 |
| 100 | $10^4$ | 0–90 | 89 |
| 10 | $10^4$ | 0–90 | — |
| 1 | $10^4$ | 0–90 | — |
| 0.1 | $10^5$ | 0 | — |

TABLE Ig(i)

Furfuryladenosine

| CONCENTRATION µM | TITER | PERCENT INHIBITION | Viability |
|---|---|---|---|
| 100 | <10 | — | 0 |
| 10 | 10³ | 90–99 | 71 |
| 1 | 10⁴ | 0–90 | 71 |
| 0.1 | 10³ | 90–99 | 88 |

TABLE Ih(i)

N⁶-Furfuryladenosine-5'-Monophosphate

| CONCENTRATION µM | TITER | PERCENT INHIBITION | Viability |
|---|---|---|---|
| 1000 | 10 | 90–99 | <50 |
| 100 | 10³ | 0–90 | 90 |
| 10 | 10⁴ | 0–90 | — |
| 1 | 10⁴ | 0–90 | — |
| 0.1 | 10⁴ | 0–90 | — |

TABLE II(i)

N⁶-Adamantyladenosine

| CONCENTRATION µM | TITER | PERCENT INHIBITION | Viability |
|---|---|---|---|
| 1000 | <10 | 99.9–99.99 | 87 |
| 100 | 10⁴ | 0–90 | — |
| 10 | 10⁴ | 0–90 | — |
| 1 | 10⁴ | 0–90 | — |
| 0.1 | 10⁴ | 0–90 | — |

A series of experiments, following the procedure outlined in Experiment 1a(I), were carried out to study the effects compounds Id, Ig and II analogues and metabolites on human T and B lymphocyte function. The results are presented in Charts Id(i), Id(ii), Ig(i), Ig(ii), II(i), II(ii) (FIGS. 18–23).

Although the present invention has been described in connection with preferred embodiments, it will be appreciated by those skilled in the art that additions, modifications, substitutions and deletions not specifically described may be made without departing from the spirit and scope of the invention defined in the appended claims.

I claim:

1. A method of treatment of a patient, either animal or human, against viral infection, the treatment comprising administering to a patient suffering from viral infection an effective dosage of a pharmaceutical formulation comprising a compound, or a physiologically acceptable salt thereof, selected from the group having the formula:

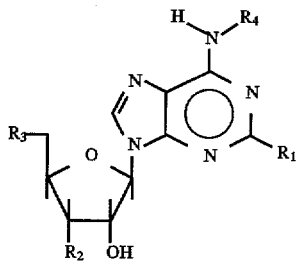

wherein:

$R_1=H$, $R_2=CH_3$, $R_3=CH_3$ and $R_4=H$, or $R_1=H$ or $CH_3S$ and $R_4=$

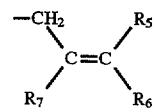

and $R_5=CH_3$ or Cl
$R_6=CH_3$, $CH_2OH$ or Cl and
$R_7=H$ or Br or $R_1=H$
and
$R_4=$

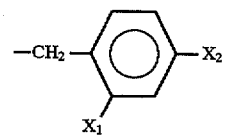

and $X_1$ and $X_2$ are independently selected from H, methyl, ethyl, hydroxyl, the halogens and carboxyl or $R_4=$

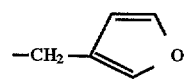

or $R_4=$

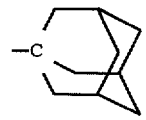

or $R_4=$

and

R$_8$=

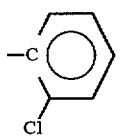

or

R$_8$=—(CH$_2$)$_7$CH$_3$ and

R$_2$=—OH and R$_3$=—OH, monophosphate, di-phosphate or triphosphate group or

R$_2$ and R$_3$ are linked to form a 3',5'-cyclic monophosphate derivative, with the proviso that R$_4$ does not equal

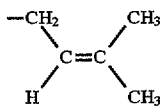

when R$_1$=H, R$_2$=OH and R$_3$=OH.

2. The method according to claim 1 wherein the patient is suffering from retroviral infection.

3. The method according to claim 2 wherein the patient is suffering from HIV infection.

4. The method according to claim 1 wherein the treatment comprises administering said formulation contained in a gelatine capsule.

5. The method according to claim 1 wherein the treatment comprises administering said formulation in unit doses of 0.01 mg. to 1000 mg.

6. The method according to claim 1 wherein the treatment comprises administering said formulation intravenously in a daily unit dose of 0.01 mg to 80 mg per kilogram of patient body weight.

7. A method of treatment of a patient, whether animal or human, suffering from a viral infection, comprising administering a pharmaceutical formulation comprising a compound selected from those recited in claim 1, wherein the treatment also comprises monitoring the degree of viral infection by measuring the amount of viral antigen in blood samples taken from the patient, to monitor the course of the viral infection while the compound is administered, so determining an effective amount of the compound.

8. The method according to claim 1, further comprising administering an effective amount of an immune system booster to the patient.

9. The method according to claim 1, wherein the patient is infected with a viral infection which has produced the AIDS syndrome.

10. The method recited in claim 1, wherein said compound has a combination of chemical groups R$_1$ to R$_4$ selected from the following combinations Ib to It:

R$_4$= 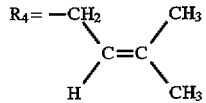

or

11. A method of treatment of a patient, either animal or human, for establishing improved immuno response for patients in which immuno-deficiency resulting from viral and/or retroviral interference is considered a future risk, the treatment comprising administering an effective dosage of a pharmaceutical formulation comprising a compound, or a physiologically acceptable salt thereof, selected from the group having the formula:

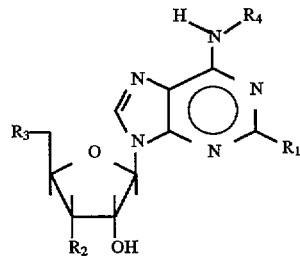

wherein:

R$_1$=H, R$_2$=CH$_3$, R$_3$=CH$_3$ and R$_4$=H, or R$_1$=H or CH$_3$S and

R$_4$=

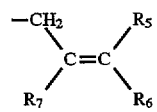

and

R$_5$=CH$_3$ or Cl

R$_6$=CH$_3$, CH$_2$OH or Cl and

R$_7$=H or Br or

R$_1$= and

R$_4$=

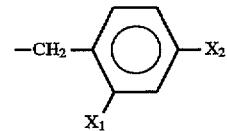

and X$_1$ and X$_2$ are independently selected from H, methyl, ethyl, hydroxyl, the halogens and carboxyl or

R$_4$=

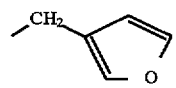

or

R$_4$=

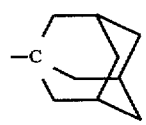

or $R_4=$

and
$R_8=$

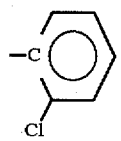

or
$R_8=-(CH_2)_7CH_3$
and $R_2=OH$ and $R_3=OH$, monophosphate, di-phosphate or triphosphate group
or $R_2$ and $R_3$ are linked to form a 3',5'-cyclic monophosphate derivative, with the proviso that $R_4$ does not equal

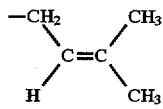

when $R_1=H$, $R_2=OH$ and $R_3=OH$.

12. A method as recited in claim 1, wherein $R_1=H$, $R_2=OH$, $R_3=$monophosphate, and

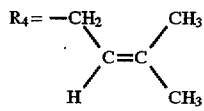

13. A method, as recited in claim 12, wherein said patient is suffering from retroviral infection.

14. A method as recited in claim 1, wherein said patient is suffering from HIV infection.

15. The method according to claim 1 wherein the patient is infected with cytomegalovirus.

16. The method according to claim 1 wherein the treatment further comprises administering an effective amount of an adenosine deaminase inhibitor to the patient.

17. The method according to claim 1, wherein the treatment comprises administering said formulation wherein the patient is a goat infected with caprine arthritis encephalitis virus.

18. The method according to claim 1 wherein the patient is infected with a Herpes virus.

19. The method according to claim 1 wherein the patient is infected with an animal virus.

20. A method of treatment of a patient, either animal or human, against a human virus, the treatment comprising administering to a patient suffering from a human virus an effective dosage of a pharmaceutical formulation comprising a compound, or a physiologically acceptable salt thereof, selected from the group having the formula:

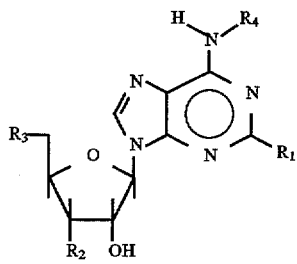

wherein Ia:

$R_1=H$, $R_2=OH$, $R_3=OH$ and
$R_4=$

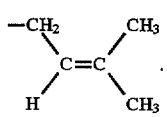

21. A method as recited in claim 20, wherein said virus is selected from HTLV and LAV.

* * * * *